(12) United States Patent
Ling

(10) Patent No.: US 10,716,824 B2
(45) Date of Patent: *Jul. 21, 2020

(54) SUBCUTANEOUS INJECTION FORMULATION FOR REDUCING BODY WEIGHT AND USES THEREOF

(71) Applicant: Caliway Biopharmaceuticals Co., Ltd., New Taipei (TW)

(72) Inventor: Yu-Fang Ling, New Taipei (TW)

(73) Assignee: Caliway Biopharmaceuticals Co., Ltd., New Taipei (TW)

( * ) Notice: Subject to any disclaimer, the term of this patent is extended or adjusted under 35 U.S.C. 154(b) by 16 days.

This patent is subject to a terminal disclaimer.

(21) Appl. No.: 16/327,466

(22) PCT Filed: Aug. 25, 2017

(86) PCT No.: PCT/IB2017/055129
§ 371 (c)(1),
(2) Date: Feb. 22, 2019

(87) PCT Pub. No.: WO2018/037384
PCT Pub. Date: Mar. 1, 2018

(65) Prior Publication Data
US 2019/0167753 A1    Jun. 6, 2019

(30) Foreign Application Priority Data

Aug. 26, 2016  (WO) ................ PCT/IB2016/055101
Aug. 26, 2016  (WO) ................ PCT/IB2016/055102

(51) Int. Cl.
| | | |
|---|---|---|
| A61K 36/00 | (2006.01) | |
| A61K 36/9066 | (2006.01) | |
| A61K 8/34 | (2006.01) | |
| A61K 8/86 | (2006.01) | |
| A61K 8/11 | (2006.01) | |
| A61Q 19/06 | (2006.01) | |
| A61P 43/00 | (2006.01) | |
| A61K 9/00 | (2006.01) | |
| A61K 9/08 | (2006.01) | |
| A61K 9/107 | (2006.01) | |
| A61K 31/05 | (2006.01) | |
| A61K 31/12 | (2006.01) | |
| A61K 36/82 | (2006.01) | |
| A61K 45/06 | (2006.01) | |
| A61K 47/44 | (2017.01) | |
| A61P 3/04 | (2006.01) | |

(52) U.S. Cl.
CPC ........... *A61K 36/9066* (2013.01); *A61K 8/11* (2013.01); *A61K 8/347* (2013.01); *A61K 8/86* (2013.01); *A61K 9/0019* (2013.01); *A61K 9/08* (2013.01); *A61K 9/107* (2013.01); *A61K 9/1075* (2013.01); *A61K 31/05* (2013.01); *A61K 31/12* (2013.01); *A61K 36/82* (2013.01); *A61K 45/06* (2013.01); *A61K 47/44* (2013.01); *A61P 3/04* (2018.01); *A61P 43/00* (2018.01); *A61Q 19/06* (2013.01)

(58) Field of Classification Search
CPC ..................................................... A61K 36/00
USPC ........................................................ 424/725
See application file for complete search history.

(56) References Cited

U.S. PATENT DOCUMENTS

| | | |
|---|---|---|
| 6,475,530 B1 | 11/2002 | Kuhrts |
| 2003/0147979 A1 | 8/2003 | Mae et al. |
| 2004/0071799 A1 | 4/2004 | Xu et al. |
| 2005/0267221 A1 | 12/2005 | Wellen |
| 2006/0188590 A1 | 8/2006 | Ono |
| 2009/0324703 A1 | 12/2009 | Frautschy et al. |
| 2017/0157195 A1 | 6/2017 | Ling |

FOREIGN PATENT DOCUMENTS

| | | |
|---|---|---|
| TW | 201707685 | 3/2017 |
| WO | WO2015081319 | 6/2015 |

OTHER PUBLICATIONS

Lampertheim, "KolliphorTMRH40 Macrogol-Glycerolhydroxystearat Ph. Eur Polyoxyl 40 Hydrogenated Castor Oil USP/NF", Dec. 2011, www.pharma-ingredients.basf.com.
Liandong Hu et al., "Enhancement of Oral Bioavailability of Curcumin by a Novel Solid Dispersion System", Dec. 2015, vol. 16, No. 6, American Association of Pharmaccutical Scientists.
Lorand Kiss et al., "Kinetic Analysis of the Toxicity of Pharmaceutical Excipients Cremophor EL and RH40 on Endothelial and Epithelial Cells", Jan. 29, 2013, Wiley Onlin Library (wileyonlinelibrary.com).
Lampertheim, "KolliphorTM ELP Macrogolglycerol ricinoleate Ph. Eur., Polyoxyl-35-castor Oil USP/NF", , Mar. 2012, Dec. 2011, www.pharma-ingredients.basf.com.
Ornchuma Naksuriya et al., "Curcumin nanoformulations: A review of Phrmaceutical proerties and preclinical studies and clinical data related to cancer treatment", Jan. 15, 2014, Elsevier Ltd.

*Primary Examiner* — Michael V Meller
(74) *Attorney, Agent, or Firm* — Polsinelli PC

(57) ABSTRACT

The present invention provides a subcutaneous injection formulation for reducing body weight. The subcutaneous injection formulation for reducing body weight comprises drug-containing micelles made of a polyoxyethylene castor oil derivative or polyoxyethylene castor oil derivatives, and a curcuminoid or curcuminoids encapsulated in the drug-containing micelles. The subcutaneous injection formulation for reducing body weight can reduce body weight and visceral fat on overweight or obese subjects, and has the advantages of low dosage, high stability, high fat tissue bioavailability, few side effects, and sustained release.

23 Claims, 14 Drawing Sheets

SUBCUTANEOUS INJECTION FORMULATION FOR REDUCING BODY WEIGHT AND USES THEREOF

FIELD OF THE INVENTION

The present invention relates to a subcutaneous injection formulation to be administered to an overweight or obese individual to reduce body weight of the individual, and, specifically, to a subcutaneous injection formulation comprising drug-containing micelles and a curcuminoid or curcuminoids encapsulated in the micelles, and the subcutaneous injection formulation is used for weight reduction.

BACKGROUND OF THE INVENTION

Obesity refers a state of a body that over-accumulates body fat which causes negative effects on health, which could cause shorter life expectancy and various health problems. According to the definition of obese by World Health Organization (WHO), individuals with the body mass index (BMI) greater than 25 are overweight and individuals with BMI greater than 30 are obesity. Some East Asian nations adopt more rigorous standards, e.g. the Ministry of Health and Welfare of Taiwan declared in April, 2002 that Taiwanese adults with BMI 27 are obese, or with 24≤BMI<27 are overweight.

Statistical data shows the population of overweight and obesity around the world is over 2.7 billion in 2014, wherein approximately 13% population were obese. The chance of these obese people who might suffer from related diseases such as, cardiovascular diseases, hyperlipidemia, diabetes, and cancers are drastically increased than average people. A research report of the WHO also indicated that among the diseases which caused risks of mortality around the world, overweight and obesity ranked $6^{th}$. Research data indicates that at least more than 3.4 million adults died of chronic diseases caused by overweight or obesity in 2013, wherein the medical burdens of 44% of diabetes and 23% of ischemic heart disease are attributable to obesity. Furthermore, the age of obese people is in a gradually falling trend. According to WHO data, there are approximately more than 40 million children under the age of five are overweight worldwide in 2011. According to a report published by the Johns Hopkins University Bloomberg School of Public Health in 2007, indicating that approximately 75% of adults in the USA would be overweight, wherein 41% of the population thereof would be classified as obese in 2015. With the rising of developing countries, the global population of obesity will rapidly increase and become one of the major prevalent diseases. The Centers for Disease Control and Prevention (CDC) of the USA indicated that the population of obese adults in the USA is more than 72 million, and 40% of global obese population is in the Asia-Pacific region. The percentage of overweight and obese adults in China was drastically increased from 25% in 2002 to 38.5% in 2010; it predicts that, in 2015, 50% to 57% of the population in China will be overweight.

Obesity is a health problem highly concerned worldwide, and studies show that the causes of obesity are highly complex with multiple factors involved. More and more evidences also show that obesity is an internal metabolic disorder disease which is not a simple problem that can be improved by self-control, but a complex symptom related to internal appetite regulation and energy metabolism. Obesity not only increases mortality rate and causes huge medical burden, but also affects the quality of life to mankind.

Though the cause of obesity is not completely identified, it is believed to be related to the factors of genetics, metabolism, biochemistry, culture, and spiritual-social. Research shows many causes of death are correlated with obesity including cancers, cardiovascular diseases, cerebrovascular diseases, diabetes, chronic lower respiratory diseases, chronic hepatic disease and liver cirrhosis, hypertensive diseases, renal disease, etc., indicating that the problem of obesity has become a highly concerned issue globally. In recent years, the prevalence of obesity has risen higher and higher, metabolic syndromes caused by metabolic abnormalities such as, high blood pressure (hypertension), high blood sugar (hyperglycemia), insulin resistance, and dyslipidemia, would accompanied by obesity, which would easily lead to diseases such as, diabetes, cardiovascular diseases, atherosclerosis, cerebrovascular disease, and cancer, which cause stroke, myocardial infarction, and even death.

The mechanisms of current synthetic drugs for losing weight can be divided into two categories, which are appetite suppression and blocking part of the intestinal absorption of dietary fat respectively. Among them, appetite suppression is the main mechanism of commercial weight loss drugs on the market in the past and nowadays. This type of drugs include Sibutramine (Reductil®), Lorcaserin, Qsymia®, and Contrave, etc, which have severe side effects and a certain degree of cardiovascular diseases risk. Taking the weight loss drug Sibutramine (Reductil®), which has been recalled from the market, for example, its market share was once as high as 70 percent; however, it was proved to increase the risks of causing cardiovascular disease. Therefore, the weight loss drugs containing Sibutramine ingredient were recalled from the markets of the EU, the United States, Australia, and Taiwan in 2010.

The weight loss drug which blocks part of the intestinal absorption of dietary fat is Orlistat; it is a specific and reversible gastrointestinal lipase inhibitor, by means of the inhibition of lipase secreted from pancreatic and intestine, the intestinal absorption of dietary fat is reduced by 25% to 30%. Due to the main mechanism of Orlistat is blocking fat absorption, gastrointestinal side effects such as oily stool, increased number of bowel movements, flatulence, etc. may occur during medication intake, and it would interfere with fat-soluble vitamin absorption; there are also some cases of severe side effects such as liver damage, and gallstones, etc., in foreign countries.

Therefore, the current synthetic drugs used for weight loss remain to have different degree of cardiovascular risks and safety concerns; the market demands a weight loss drug that is safer, with low side effects, without cardiovascular risk concerns, could effectively reduce weight and body fat, and could also reduce cardiovascular risk at the same time.

The document "Dietary Polyphenols and Obesity" published by Mohsen Meydani and others discloses that the total body weight gain of rat can be reduced through oral intake of curcumin. However, the oral intake dosage of curcumin disclosed in that document is high as 250 to 10000 mg/kg, and its effect on weight loss is limited.

Therefore, in the market, there is still a need for a weight reduction pharmaceutical composition which can effectively reduce body weight, with low dosage, low side-effects, and good safety. Under the high demand from both consumers and doctors, the development of weight reduction pharmaceutical composition to break through the limitation of current technologies shall be the problem need to be desperately discussed and solved.

Non-Patent Reference

Mohsen Meydani et al, "Dietary Polyphenols and Obesity", Nutrients, 2010, 2:735-751.

SUMMARY OF THE INVENTION

In view of the deficiency of prior arts, the present invention provides a pharmaceutical composition for reducing body weight, wherein the pharmaceutical composition comprises drug-containing micelles formed from a polyoxyethylene castor oil derivative or polyoxyethylene castor oil derivatives and a curcuminoid or curcuminoids encapsulated in the drug-containing micelles. The pharmaceutical composition for reducing body weight can be used to reduce body weight, and has the advantages of low dosage, high stability, low side effects, and sustained release.

The present invention can promote apoptosis on adipocytes of the whole body after administration, thereby to achieve the goal of reducing body weight. The present invention solves the problems in the prior arts, such as high dosage and many side effects, to a large extent; and the effect of body weight reduction is significantly better than oral administered weight loss drugs. The present invention is suitable for subcutaneous injection or subcutaneous fat layer injection administration to an overweight or obese subject without the need or assistance of any surgery or equipment. Preferably, it is administered to a subject whose BMI is greater than or equal to 24; preferably it is administered to a subject whose BMI is greater than 25; preferably it is administered to a subject whose BMI is greater than or equal to 27; and preferably, it is administered to a subject whose BMI is greater than 30.

In the present invention, the term "overweight" refers to that the BMI of an adult is greater than or equal to 24 and less than 27; and the term "obese" refers to that the BMI of an adult is greater than or equal to 27. Preferably, the term "overweight" refers to that the BMI of an adult is greater than 25; and the term "obese" refers to that the BMI of an adult is greater than 30.

In the present invention, the term "turmeric extract" refers to a mixture of ingredients of turmeric which is obtained through extraction by any solvent and any extraction method, commercially available turmeric extract, any mixture containing at least 75% (wt %) of curcumin, any mixture containing at least 75% (wt %) of a curcuminoid or curcuminoids, or commercially available curcumin.

In the present invention, the term "resveratrol" refers to resveratrol obtained from extraction of natural plants or commercially available resveratrol. Preferably, the purity of resveratrol is 90% to 100% (wt %).

In the present invention, the term "green tea extract" refers to a mixture of ingredients of green tea extracted by any solvent and any extraction method or commercially available green tea extract, and, preferably, any mixture containing at least 45% (weight percentage) of epigallocatechin gallate (EGCG), any mixture containing at least 90% (weight percentage) of catechins, or commercially available epigallocatechin gallate (EGCG).

In the present invention, the term "micelle" refers to a microstructure formed from a polyoxyethylene castor oil derivative or polyoxyethylene castor oil derivatives, each polyoxyethylene castor oil derivative molecule has a hydrophilic end and a hydrophobic (lipophilic) end, and the polyoxyethylene castor oil derivative molecules are arranged in a way that the hydrophilic ends face outward and the hydrophobic (lipophilic) ends face inward to form the microstructure. Preferably, the microstructure is a spherical structure, a spheroidal structure, or other microstructural structures.

In the present invention, the term "drug-containing micelles" refer to micelles containing a curcuminoid or curcuminoids. Preferably, drug-containing micelles refer to micelles containing curcumin; and, that is, drug-containing micelles refer to micelles encapsulating or containing a curcuminoid or curcuminoids. Preferably, drug-containing micelles refer to micelles encapsulating or containing curcumin.

Preferably, the drug-containing micelles are evenly distributed in the pharmaceutical composition.

In the pharmaceutical composition of the present invention, when the total concentration of a curcuminoid or curcuminoids encapsulated in the drug-containing micelles is expressed in mg/g, it represents the total milligrams of a curcuminoid or curcuminoids in all of the drug-containing micelles contained in per gram of the pharmaceutical composition.

In the pharmaceutical composition of the present invention, the total concentration of a curcuminoid or curcuminoids encapsulated in the drug-containing micelles may be measured by for example the procedure described as follows: Filtering the pharmaceutical composition through a 0.2 µm filter membrane to obtain a filtrate and a curcuminoid or curcuminoids precipitations which are not encapsulated in drug-containing micelles; Obtaining a sample solution by diluting the filtrate with DMSO to make the drug-containing micelles in the filtrate be dissolve by DMSO, and therefore further causing the curcuminoid or curcuminoids originally encapsulated in the drug-containing micelles to be released into the sample solution; Determining the concentration of the curcuminoid or curcuminoids in the sample solution by high performance liquid chromatography (HPLC; e.g. HPLC-UV); and calculating the total concentration of the curcuminoid or curcuminoids encapsulated in the drug-containing micelles in the pharmaceutical composition utilizing the concentration of the curcuminoid or curcuminoids in the sample solution.

In the present invention, the term "first drug-containing micelles" refer to the micelles containing a curcuminoid or curcuminoids; and, preferably, the drug-containing micelles refer to the micelles containing curcumin. That is, the first drug-containing micelles refer to the micelles encapsulating or containing the curcuminoid or curcuminoids; and, preferably, the first drug-containing micelles refer to the micelles encapsulating or containing curcumin.

In the present invention, the term "second drug-containing micelles" refer to the micelles containing resveratrol. That is, the second drug-containing micelles refer to the micelles encapsulating or containing resveratrol.

In the present invention, the term "curcuminoid" is the generic term for curcumin, demethoxycurcumin, and bisdemethoxycurcumin.

In the present invention, the term "catechins" is the generic term for epigallocatechin gallate, epicatechin, epicatechin gallate, epigallocatehchin, gallocatechin gallate, gallocatechin, catechin gallate, catechin.

In the present invention, the term "state without precipitations", as used herein, refers to a state in which there is no precipitation which can be observed with the naked eye, that is, without the assistance of artificial instruments.

In the present invention, the pharmaceutically acceptable aqueous solution is at least one of water for injection, aqueous solution for injection, normal saline, and other pharmaceutically acceptable aqueous solution, or a combination thereof.

In the present invention, the local anesthetic is at least one of amides, para-aminobenzoic acid esters, amino ethers, and other local anesthetics, or a combination thereof. Preferably, one of the amides is at least one of dibucaine, lidocaine, mepivacaine HCl, bupivacine HCl, pyrrocaine HCl, prilocaine HCl, digammacaine, and oxethazaine, or a combination thereof. Preferably, one of the para-aminobenzoic acid esters is at least one of butacaine, dimethocaine, and tutocaine, or a combination thereof. Preferably, one of the amino ethers is at least one of quinisocaine and pramocaine, or a combination thereof.

In the present invention, the antioxidant is at least one of beta-carotene, lutein, lycopene, bilirubin, vitamin A, vitamin C (ascorbic acid), vitamin E, uric acid, nitric oxide, nitroxide, pyruvate, catalase, superoxide dismutase, glutathione peroxidases, N-acetyl cysteine, naringenin, and other antioxidants, or a combination thereof.

In the present invention, the pharmaceutical composition maintains at a state without precipitations for at least 24 hours when it is subjected to accelerated stability test at 25° C.±2° C., relative humidity (RH) 60%±5%, and in the absence of direct light.

Or, the pharmaceutical composition maintains at a state without precipitations for at least 6 months when it is subjected to accelerated stability test at 25° C.±2° C., relative humidity (RH) 60%±5%, and in the absence of direct light.

In the present invention, when the concentration of cremophor ELP is indicated in the form of percentages, it represents the grams of cremophor ELP contained in per 100 ml of solution.

The present invention provides a use of a pharmaceutical composition for preparing a subcutaneous injection formulation to be administered to an overweight or obese subject to reduce body weight of the subject; the pharmaceutical composition comprises:

a pharmaceutically acceptable aqueous solution;

a plurality of drug-containing micelles which are evenly distributed in the pharmaceutically acceptable aqueous solution; wherein, each of the drug-containing micelles is a microstructure formed from a pharmaceutically acceptable polyoxyethylene castor oil derivative, and the hydrophilic-lipophilic balance value (HLB value) of the polyoxyethylene castor oil derivative is greater than 10; and a curcuminoid or curcuminoids encapsulated in the drug-containing micelles;

wherein, a total concentration of the curcuminoid or curcuminoids encapsulated in the drug-containing micelles is 0.2 to 120 mg/g.

Preferably, the pharmaceutically acceptable aqueous solution further comprises a catechins ingredient.

Preferably, the total concentration of the curcuminoid or curcuminoids in the drug-containing micelles is 0.4 to 167 mg/g; or, the total concentration of the curcuminoid or curcuminoids in the drug-containing micelles is 0.5 to 111 mg/g; or, the total concentration of the curcuminoid or curcuminoids in these drug-containing micelles is 2 to 91 mg/g.

Preferably, the concentration of the catechins ingredient is 0.04 to 835 mg/g.

Preferably, the concentration of the catechins ingredient is 0.15 to 733 mg/g.

Preferably, the catechins ingredient is at least one of epigallocatechin gallate, epicatechin, epicatechin gallate, epigallocatechin, gallocatechin gallate, gallocatechin, catechin gallate, and catechin, or a combination thereof.

Preferably, the weight ratio of the curcuminoid or curcuminoids to the catechins ingredient in the pharmaceutical composition is 50:1 to 1:20.

Preferably, the weight ratio of the curcuminoid or curcuminoids to the catechins ingredient in the pharmaceutical composition is 30:1 to 1:10; or, the weight ratio of the curcuminoid or curcuminoids to the catechins ingredient in the pharmaceutical composition is 10:1 to 1:4; or, the weight ratio of the curcuminoid or curcuminoids to the catechins ingredient in the pharmaceutical composition is 7:1 to 1:4.

Preferably, the diameter of the drug-containing micelles is 3 to 50 nm.

Preferably, the diameter of the drug-containing micelles is 5 to 20 nm.

Preferably, the administration dosage of the subcutaneous injection formulation is 0.15 to 40 mg per kilogram for injection.

Preferably, the administration dosage of the subcutaneous injection formulation is 0.25 to 25 mg per kilogram for injection.

Preferably, administration frequency of the subcutaneous injection formulation at an administration site is 1 to 6 times every 1 to 90 days.

Preferably, one shot or more of the subcutaneous injection formulation is administered at the administration site per administration.

Preferably, the weight ratio of the curcuminoid or curcuminoids to the polyoxyethylene castor oil derivative is 1:5 to 1:750.

Preferably, the weight ratio of the curcuminoid or curcuminoids to the polyoxyethylene castor oil derivative is 1:20 to 1:150.

Preferably, the polyoxyethylene castor oil derivative is at least one of Kolliphor ELP (also known as Cremophor ELP), Cremophor RH 40, and other polyoxyethylene castor oil derivatives, or a combination thereof.

Preferably, the pharmaceutical composition further comprises at least one of a cosolvent, a suspending agent, and an oil phase excipient, or a combination thereof.

Preferably, the microstructure is formed from the polyoxyethylene castor oil derivative and at least one of the oil phase excipient and the cosolvent.

Preferably, the curcuminoid is curcumin.

The present invention further provides a use of a pharmaceutical composition for preparing a subcutaneous injection formulation to be administered to an overweight or obese subject to reduce body weight of the subject; the pharmaceutical composition comprises:

a plurality of first drug-containing micelles, and a plurality of second drug-containing micelles, in which, each of the first drug containing micelles is a microstructure which is formed from a pharmaceutically acceptable polyoxyethylene castor oil derivative, and the hydrophilic-lipophilic balance value (HLB value) of the polyoxyethylene castor oil derivative is greater than 10;

a curcuminoid or curcuminoids encapsulated in the first drug-containing micelles; and resveratrol encapsulated in the second drug-containing micelles;

wherein, the total concentration of the curcuminoid or curcuminoids encapsulated in the first drug-containing micelles is 0.2 to 167 mg/g.

Preferably, the total concentration of resveratrol encapsulated in the second drug-containing micelles is 0.2 to 733 mg/g.

Preferably, the sum of the total concentration of the curcuminoid or curcuminoids encapsulated in the first drug-containing micelles and the total concentration of resveratrol encapsulated in the second drug-containing micelles is 0.4 to 900 mg/g.

Preferably, the ratio of the total weight of the curcuminoid or curcuminoids encapsulated in the first drug-containing micelles to the total weight of resveratrol encapsulated in the second drug-containing micelles is 50:1 to 1:30.

Preferably, the ratio of the total weight of the curcuminoid or curcuminoids encapsulated in the first drug-containing micelles to the total weight of resveratrol encapsulated in the second drug-containing micelles is 30:1 to 1:10.

Preferably, the ratio of the total weight of the curcuminoid or curcuminoids encapsulated in the first drug-containing micelles to the total weight of resveratrol encapsulated in the second drug-containing micelles is 20:1 to 1:20.

Preferably, the ratio of the total weight of the curcuminoid or curcuminoids encapsulated in the first drug-containing micelles to the total weight of resveratrol encapsulated in the second drug-containing micelles is 20:1 to 1:8.

Preferably, the administration dosage of the subcutaneous injection formulation is 0.15 to 40 mg per kilogram for injection.

Preferably, the administration dosage of the subcutaneous injection formulation is 0.25 to 25 mg per kilogram for injection.

Preferably, the administration dosage of the subcutaneous injection formulation is 0.4 to 25 mg per kilogram for injection.

Preferably, the administration dosage of the subcutaneous injection formulation is 0.5 to 20 mg per kilogram for injection.

Preferably, the administration dosage of the subcutaneous injection formulation is 0.02 to 20 mg per $cm^2$ for injection.

Preferably, the administration dosage of the subcutaneous injection formulation is 0.04 to 16 mg per $cm^2$ for injection.

Preferably, the administration frequency of the subcutaneous injection formulation is 1 to 12 times at the administration site for every 1 to 90 days.

Preferably, the administration frequency of the subcutaneous injection formulation is 1 to 6 times at the administration site for every 1 to 90 days.

Preferably, the administration frequency of the subcutaneous injection formulation is 1 to 6 times at the administration site for every 1 to 60 days.

Preferably, the ratio of the total weight of the curcuminoid or curcuminoids encapsulated in the first drug-containing micelles to the total weight of the polyoxyethylene castor oil derivative is 1:5 to 1:750.

Preferably, the pharmaceutical composition further comprises at least one of a cosolvent, a suspending agent, and an oil phase excipient, or a combination thereof.

Preferably, the microstructure is formed from the polyoxyethylene castor oil derivative and at least one of the oil phase excipient and the cosolvent.

Preferably, each of the second drug-containing micelles is a second microstructure formed from a pharmaceutically acceptable second polyoxyethylene castor oil derivative, and the hydrophilic-lipophilic balance value (HLB value) of the second polyoxyethylene castor oil derivative is greater than 10.

Preferably, the polyoxyethylene castor oil derivative is at least one of Cremophor ELP, Cremophor RH 40, and other polyoxyethylene castor oil derivatives, or a combination thereof; or the second polyoxyethylene castor oil derivative is at least one of Kolliphor ELP (also known as Cremophor ELP), Cremophor RH 40, and other polyoxyethylene castor oil derivatives, or a combination thereof.

Preferably, the curcuminoid is curcumin.

Preferably, the pharmaceutical composition further comprises a cosolvent to increase the solubility of drugs.

Preferably, the cosolvent is at least one of polyethylene glycol, propylene glycol, ethanol, and other cosolvents, or a combination thereof.

Preferably, the polyethylene glycol is at least one of PEG 200, PEG 400, PEG 600, and other polyethylene glycols, or a combination thereof.

Preferably, the pharmaceutical composition further comprises a suspending agent to reduce the sedimentation rate of drugs or micelles.

Preferably, the suspending agent is at least one of sodium alginate, glycerol, carboxymethylcellulose sodium, mannitol, and other suspending agents, or a combination thereof.

Preferably, the pharmaceutical composition further comprises an oil phase excipient to increase the stability of the pharmaceutical composition and the solubility of drugs.

Preferably, the oil phase excipient is at least one of unsaturated fatty acids, glycerol, triglycerides, and other oil phase excipients, or a combination thereof.

Preferably, the unsaturated fatty acids include at least one of oleic acid, castor oil, sesame oil, cottonseed oil, soybean oil, safflower oil, corn oil, and other unsaturated fatty acids, or a combination thereof.

Preferably, the triglycerides include at least one of medium chain triglycerides, and other triglycerides, or combination thereof.

Preferably, the pharmaceutically acceptable aqueous solution comprises a local anesthetic.

Preferably, the pharmaceutically acceptable aqueous solution comprises an antioxidant.

The present invention further provides a method for reducing the body weight of an overweight or obese subject, comprising administering a subcutaneous injection formulation to the overweight or obese subject, wherein, the subcutaneous injection formulation comprises:
a pharmaceutically acceptable aqueous solution;
a plurality of drug-containing micelles, which is evenly distributed in the pharmaceutically acceptable aqueous solution, wherein, each of the drug-containing micelles is a microstructure formed from a pharmaceutically acceptable polyoxyethylene castor oil derivative, and the hydrophilic-lipophilic balance value (HLB value) of the polyoxyethylene castor oil derivative is greater than 10; and
a curcuminoid or curcuminoids encapsulated in the drug-containing micelles;
wherein, the total concentration of the curcuminoid or curcuminoids encapsulated in the drug-containing micelles is 0.2 to 167 mg/g.

Preferably, the pharmaceutically acceptable aqueous solution further comprises a catechins ingredient.

Preferably, the weight ratio of the curcuminoid or curcuminoids to the catechins ingredient in the subcutaneous injection formulation is 50:1 to 1:20.

Preferably, the weight ratio of the curcuminoid or curcuminoids to the catechins ingredient in the subcutaneous injection formulation is 30:1 to 1:10; or, the weight ratio of the curcuminoid or curcuminoids to the catechins ingredient in the subcutaneous injection formulation is 10:1 to 1:4; or, the weight ratio of the curcuminoid or curcuminoids to the catechins ingredient in the subcutaneous injection formulation is 7:1 to 1:4.

The present invention further provides a method for reducing the body weight of an overweight or obese subject, comprising administering a subcutaneous injection formulation to the overweight or obese subject, wherein, the subcutaneous injection formulation comprises:

a plurality of first drug-containing micelles and a plurality of second drug-containing micelles wherein each of the first drug-containing micelles is a microstructure formed from a pharmaceutically acceptable polyoxyethylene castor oil derivative, and the hydrophilic-lipophilic balance value (HLB value) of the polyoxyethylene castor oil derivative is greater than 10;

a curcuminoid or curcuminoids encapsulated in the first drug-containing micelles; and resveratrol encapsulated in the second drug-containing micelles;

wherein, the total concentration of a curcuminoid or curcuminoids encapsulated in the first drug-containing micelles is 0.2 to 167 mg/g.

DETAILED DESCRIPTION OF THE INVENTION

Figure 1A:
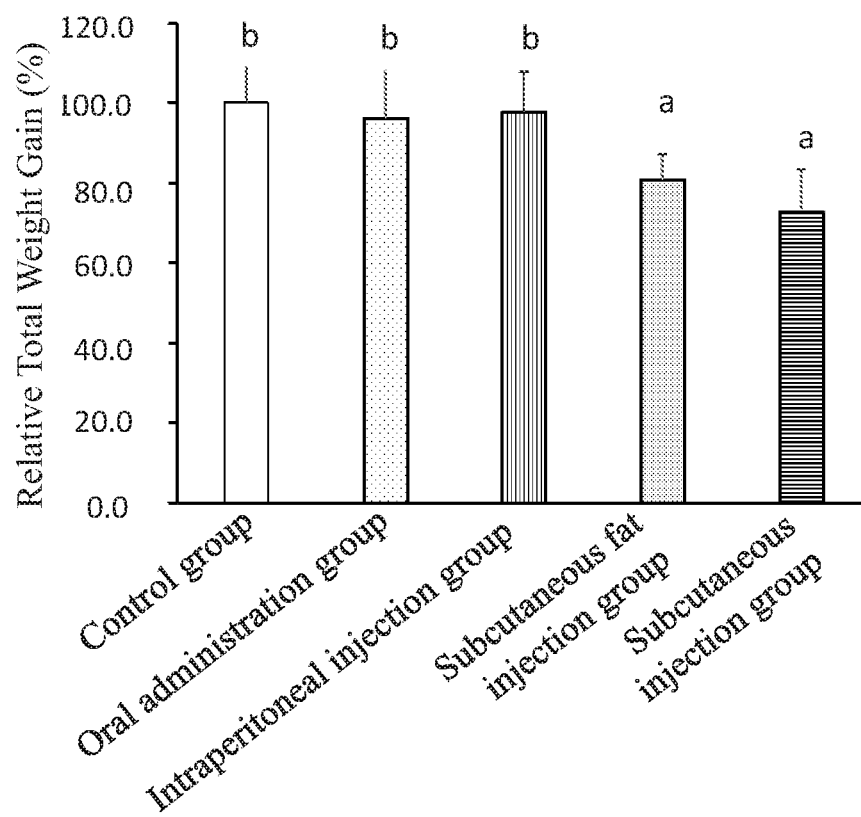
FIG. 1A: A bar graph showing the effect of curcumin-green tea extract complex pharmaceutical composition administered by different routes on the relative total weight gain of rats.

In view of the deficiency of prior arts, the inventor, according to the study results and experience for years, believes that it is possible to establish a kind of pharmaceutical composition containing low dosage of curcuminoid, which can reduce body weight and visceral fat of a subject, and has the advantages of high stability, high fat tissue bioavailability, low side effects, and sustained release.

The followings are detailed descriptions of the embodiments of the present invention, and the technology and features of the present invention. However, the embodiments are not intended to limit the present invention, and, to one skilled in the art, any alteration or modification that does not depart from the spirits disclosed herein should be within the scope of the claims of the present invention.

In the description of the following embodiments, "green tea extract" means a mixture containing at least 45% (wt %) of epigallocatechin gallate (EGCG) or any kind of mixture containing at least 90% (wt %) of catechins.

Experiment 1: The Effects of Low Dosage Pharmaceutical Compositions Administrated by Different Routes on the Amount of the Visceral Fat and the Body Weight of Rats Preparation of curcumin-green tea extract oral liquid: An appropriate amount of curcumin and green tea extract were added into an appropriate amount of sterile reverse osmosis water, and stirred well, and the curcumin-green tea extract oral liquid was obtained, in which the total concentration of curcumin and green tea extract was 100 mg/mL and the weight ratio of curcumin to green tea extract was 4:1.

Preparation of curcumin-green tea extract complex pharmaceutical composition: 0.8 g of curcumin and 150 to 200 mL of dichloromethane were mixed, and stirred at 150 to 500 rpm at room temperature until curcumin dissolved completely. 30 g of Kolliphor ELP (also known as ELP) was added, and stirred well at 100 to 300 rpm to volatilize the dichloromethane. Once the dichloromethane volatilized completely, normal saline for injection was slowly added to obtain a total volume of 200 mL, wherein, the normal saline for injection comprised 0.2 g of green tea extract. The solution was mixed well to obtain the curcumin-green tea extract complex pharmaceutical composition comprising ELP. The curcumin-green tea extract complex pharmaceutical composition comprising ELP comprised drug-containing micelles, the total concentration of curcumin and green tea extract was 5 mg/mL, the weight ratio of curcumin to green tea extract was 4:1, and the concentration of Kolliphor ELP was about 15%.

Six-week-old male Sprague-Dawley rats were used for the experiment. 24 rats were fed with normal diet (product of Research Diets, Inc.) for a week to make the body weight of the rats reach 175 to 200 g, then fed with high-fat diet (Research Diets, Inc.; # D12492) for 14 days to be induced into an obese animal mode and their body weight was allowed to increase to 400 to 450 g, and, thereafter, the rats were randomly assigned into five groups, i.e. control group, oral administration group (PO group), intraperitoneal injection group (IP group), subcutaneous injection group (SC group), and subcutaneous fat injection group (IA group)

respectively; there was no statistical difference in the body weight among the groups. Wherein, the control group comprised of 8 rats, and each of the oral administration group, the intraperitoneal injection group, the subcutaneous injection group, and the subcutaneous fat injection group comprised of 4 rats. The body weight of each rat was recorded before the test, defined as "pre-experimental body weight" of each rat.

Oral administration group (PO group): The curcumin-green tea extract oral liquid was administered via oral gavage to the rats from day 1 of the experiment, once per day, consistently for 14 days, with a dosage of 2 mL per kilogram of body weight (2 mL/kg) per administration via oral gavage, to allow that the administration dosage to be administered each time was 160 mg of curcumin and 40 mg of green tea extract per kilogram of body weight (the total concentration of curcumin and green tea extract administered per kilogram of body weight was 2 mL/kg×100 mg/mL=200 mg/kg, in which, the weight ratio of curcumin to green tea extract was 4:1, and accordingly the curcumin administered per kilogram of body weight was 200 mg/kg÷5×4=160 mg, and the green tea extract administered per kilogram of body weight was 200 mg/kg÷5×1=40 mg).

Intraperitoneal injection group (IP group): The curcumin-green tea extract complex pharmaceutical composition was administered to the rats via intraperitoneal injection, and the administration sites were the right portion of the abdomen of rats. One administration was performed on the day 1, day 3, day 5, day 7, day 9, day 11, for a total of 6 administrations, with the dosage of 4 mL per kilogram of body weight (4 mL/kg) for injection per administration, to allow that the administration dosage to be administered each time was 16 mg of curcumin and 4 mg of green tea extract per kilogram of body weight (the total concentration of curcumin and green tea extract administered per kilogram of body weight was 4 mL/kg×5 mg/mL=20 mg/kg, in which, the weight ratio of curcumin to green tea extract was 4:1, and hence the curcumin administered per kilogram was 20 mg/kg÷5×4=16 mg, and the green tea extract administered per kilogram of body weight was 20 mg/kg÷5×1=4 mg).

Subcutaneous injection group (SC group): The curcumin-green tea extract complex pharmaceutical composition was administered to the rats via subcutaneous injection, and the administration sites were behind the ear on the back, above the scapula, or below the scapula of rats. One administration was performed on the day 1, day 3, day 5, day 7, day 9, and day 11, for a total of 6 administrations, with the dosage of 4 mL per kilogram of body weight (4 mL/kg) for injection per administration, to allow that the administration dosage to be administered each time was 16 mg of curcumin and 4 mg of green tea extract per kilogram of body weight.

Subcutaneous fat injection group (IA group): The curcumin-green tea extract complex pharmaceutical composition was administered to the rats via subcutaneous fat injection, and the administration sites were the bilateral lower inguinal fat pads of the rats. One administration was performed on the day 1, day 3, day 5, day 7, day 9, day 11, for a total of 6 administrations, with the dosage of 4 mL per kilogram of body weight (4 mL/kg) for injection per administration, to allow that the administration dosage to be administered each time was 16 mg of curcumin and 4 mg of green tea extract per kilogram of body weight.

Control group: The control group was divided into oral administration control group and injection control group, with 4 rats in each group. Sterile reverse osmosis water was administered to the rats in the oral administration control group via oral gavage, once per day via oral gavage, and the dosage for oral gavage was 2 mL per kilogram of body weight (2 mL/kg) via oral gavage. The administration via oral gavage was consistent for 14 days. Normal saline for injection was administered to the rats in the injection control group via injection, and one administration was performed on day 1, day 3, day 5, day 7, day 9, and day 11 in the experiment, for a total of 6 administrations. The dosage for each injection was 4 mL per kilogram of body weight (4 mL/kg). The data of the oral administration control group and injection control group was combined into the control group because the results indicate that there was no significant difference in the data between the two groups.

The rats were fed with high-fat diet for the entire duration of the experiment. Their weight changes were recorded daily, and food and water consumption was recorded weekly. The experiment lasted for 20 days, and the rats were euthanized by $CO_2$ on day 21. And, the body weight of each rat was recorded and defined as the "post-experimental body weight" of each rat.

The "total weight gain" of each rat was obtained by subtracting its "pre-experimental body weight" from its "post-experimental body weight". The "relative total weight gain" was obtained by dividing the total weight gain of rats in each group by the total weight gain of rats in the control group.

The epididymal fat, perinephric fat and mesenteric fat of rats were each dissected and weighed, and the sum thereof is the weight of visceral fat. The weight of visceral fat of each group was divided by the weight of visceral fat of the control group to obtain the "relative weight of the visceral fat".

The data were presented as mean±SD and analyzed by one-way ANOVA. Statistical results were shown as letters. Different letter symbols indicate statistically significant difference ($p<0.05$), and identical letter symbols indicate no statistically significant difference ($p>0.05$).

Figure 1B:
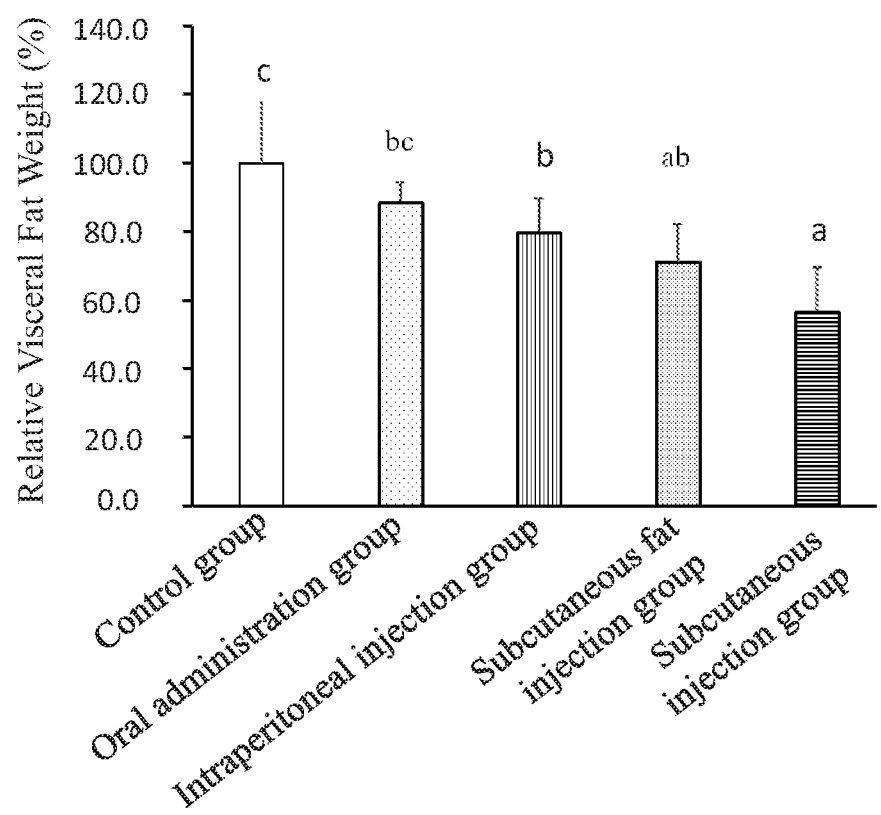
FIG. 1B: A bar graph showing the effect of curcumin-green tea extract complex pharmaceutical composition administered by different routes on the relative weight of visceral fat of rats.

Please refer to FIG. 1A and FIG. 1B. FIG. 1A is a bar graph showing the effect of curcumin-green tea complex pharmaceutical composition administered by different routes on the relative total weight gain of rats. FIG. 1B is a bar graph showing the effect of curcumin-green tea extract complex pharmaceutical composition administered by different routes on the relative visceral fat weight of rats.

Results of FIG. 1A indicate that, the relative total weight gain of rats in the control group was 100.1±9.4%, the relative total weight gain of rats in the oral administration group was 96.2±12.4%, the relative total weight gain of rats in intraperitoneal injection group was 97.8±10.1%, the relative total weight gain of rats in subcutaneous fat injection group was 80.8±6.5%, the relative total weight gain of rats in subcutaneous injection group was 72.9±10.6%. Among them, there was no significant difference in the relative total weight gain between the rats in the oral administration group and the rats in the control group, indicating that the body weight of the rats cannot be reduced by administering curcumin-green tea extract complex pharmaceutical composition via oral administration; there was no significant difference in the relative total weight gain between the rats in intraperitoneal injection group and the rats in the control group, indicating that the body weight of the rats also cannot be reduced by administering curcumin-green tea extract complex pharmaceutical composition via intraperitoneal injection; the relative total weight gain of the rats in subcutaneous fat injection group was significantly different ($p<0.05$) from that of the control group, and the relative total weight gain of rats in subcutaneous fat injection group was reduced by 19.3%; the relative total weight gain of the rats in subcutaneous injection group was significantly different (p<0.05) from that of the control group, and the relative total weight gain of rats in subcutaneous injection group was reduced by 27.2%. The results indicate that by administering low dosage curcumin-green tea extract complex pharmaceutical composition via subcutaneous fat injection or subcutaneous injection can effectively reduce the body weight of overweight or obese rats, and the effect of administration via subcutaneous injection is the best.

Results of FIG. 1B indicate that, the relative visceral fat weight of rats in the control group was 100.0±18.8%, the relative visceral fat weight of rats in the oral administration group was 88.3±5.9%, the relative visceral fat weight of rats in intraperitoneal injection group was 79.7±10.1%, the relative visceral fat weight of rats in the subcutaneous fat injection group was 71.1±11.0%, the relative visceral fat weight of rats in the subcutaneous injection group was 56.5±13.1%. Among them, there was no significant difference in the amount of relative visceral fat between the rats in the control group and the rats in the oral administration group, indicating that the visceral fat of rats cannot be reduced by administering curcumin-green tea extract complex pharmaceutical composition via oral administration; the relative visceral fat weight of rats in intraperitoneal injection group was significantly different (p<0.05) from that of the control group, however the relative visceral fat weight of the rats in intraperitoneal injection group was only decreased by 20.3%; the relative visceral fat weight of rats in subcutaneous fat injection group was significantly different (p<0.05) from that of the control group, and the relative visceral fat weight of rats in subcutaneous fat group was reduced by 28.9%; and the relative visceral fat weight of rats in subcutaneous injection group was significantly different (p<0.05) from that of the control group, and the relative visceral fat weight of rats in the subcutaneous injection group was reduced by 43.5%. The results indicate that the relative visceral fat weight of overweight or obese rats can be reduced by administration of low dosage curcumin-green tea extract complex pharmaceutical composition via intraperitoneal injection, subcutaneous fat injection, or subcutaneous injection, wherein, the effect of administration via subcutaneous fat injection and administration via subcutaneous injection is preferred, and the fat reduction via subcutaneous injection is even more significant than via intraperitoneal injection (p<0.05).

Traditionally generally speaking, drugs can reach all parts of the body of rats faster via intraperitoneal injection than via subcutaneous injection to further achieve the effect of, for example, weight reduction or visceral fat reduction, on the whole body. However, the results of the present invention indicates that, in comparison with intraperitoneal injection, administration of the low dosage of the pharmaceutical composition of the present invention to overweight or obese rats via subcutaneous injection can more remarkably achieve the effect of weight reduction and visceral fat reduction significantly (p<0.05), that is, administering the low dosage of the pharmaceutical composition of the present invention via subcutaneous injection has unanticipated effects.

Experiment 2: Effect of Curcumin-Green Tea Extract Complex Pharmaceutical Composition on Different Groups The curcumin-green tea extract complex pharmaceutical was administered separately to rats that is normal and obese to evaluate the effect of curcumin-green tea complex pharmaceutical composition on different groups of rats.

Preparation of curcumin-green tea extract complex pharmaceutical composition: 0.6 g of curcumin and 150 to 200 mL of dichloromethane were mixed, and stirred at 150 to 500 rpm at room temperature until curcumin dissolved completely. 30 g of Kolliphor ELP (also known as ELP) was added and stirred well at 100 to 300 rpm to volatilize the dichloromethane. Once the dichloromethane volatilized completely, normal saline for injection was slowly added to obtaining a total volume of 200 mL, wherein, the normal saline for injection comprised 0.4 g of green tea extract. The solution was mixed well to obtain the curcumin-green tea extract complex pharmaceutical composition. The curcumin-green tea extract complex pharmaceutical composition comprising ELP comprised drug-containing micelles, the total concentration of curcumin and green tea extract was 5 mg/mL, the weight ratio of curcumin to green tea extract is 3:2, and the concentration of Kolliphor ELP was about 15%.

Six-week-old male Sprague-Dawley rat were used for the experiment. 16 rats were fed with normal diet for a week to make the body weight of the rats reach 175 to 200 g. The rats were divided into 4 groups, that is, normal diet control group, high-fat diet control group, normal diet-green tea extract complex pharmaceutical composition, and high-fat diet-green tea extract complex pharmaceutical composition. Afterwards, the rats in the normal diet control group and the normal diet-green tea extract complex pharmaceutical composition group were continuously fed with normal diet for 14 days, and, at the same time, the rats in the high-fat diet control group and the high-fat diet-green tea extract complex pharmaceutical composition were fed with high-fat diet for 14 days, to induce the rats in the high-fat diet control group and the high-fat diet-green tea extract complex pharmaceutical composition group into an obese animal mode and their body weight was allowed to increase to 400 to 450 g. Thereafter, subcutaneous injections were administered as follows.

For the normal diet control group and the high-fat diet control group: normal saline was administered to the rats via subcutaneous injection, and the administration sites were behind the ear on the back, above the scapula, or below the scapula of rats. One administration was performed on the day 1, day 3, day 5, day 7, day 9, and day 11, for a total of 6 administrations, and the dosage for injection was 4 mL per kilogram of body weight (4 mL/kg).

For the normal diet-green tea extract complex pharmaceutical composition group and the high-fat diet-green tea extract complex pharmaceutical composition group: the curcumin-green tea extract complex pharmaceutical composition was administered to the rats via subcutaneous injection, the administration sites were behind the ear on the back, above the scapula, or below the scapula of rats. One administration was performed on the day 1, day 3, day 5, day 7, day 9, and day 11, for a total of 6 administrations, and the dosage for injection was 4 mL per kilogram of body weight (4 mL/kg), to allow that the administration dosage to be administered each time was 12 mg of curcumin and 8 mg of resveratrol per kilogram of body weight (The total concentration of curcumin to green tea extract administered per kilogram of body weight was 4 mL/kg×5 mg/mL=20 mg/kg, wherein, the weight ratio of curcumin to green tea extract was 3:2; and, hence, the curcumin administered per kilogram of body weight was 20 mg/kg÷5×3=12 mg, and the green tea extract administered per kilogram of body weight was 20 mg/kg÷5×2=8 mg).

Normal diet was consistently given to the rats in the normal diet control group and the normal diet-green tea extract complex pharmaceutical composition during experiment period, and high-fat diet was given to the rats in the high-fat diet control group and the high-fat diet-green tea extract complex pharmaceutical composition group. The experiment was performed for a total of 20 days, and the rats were sacrificed with $CO_2$ on day 21.

Experimental results indicate that, in comparison with the normal diet control group, both of the relative total weight gain and relative visceral fat weight of the rats in the normal diet-green tea extract complex pharmaceutical composition group did not reduced significantly, indicating that the pharmaceutical composition of the present invention cannot reduce body weight of normal rats, and cannot reduce visceral fat weight of normal rats. In comparison with the high-fat diet control group, both of the relative total weight gain and the relative visceral fat weight of the rats in the high-fat diet-green tea extract complex pharmaceutical composition group reduced significantly ($p<0.05$), indicating that the pharmaceutical composition of the present invention can reduce body weight of overweight or obese rats, and can also reduce the visceral fat weight of overweight or obese rats.

The results above indicates that the pharmaceutical compositions of the present invention only have the effect of body weight and visceral fat reduction on certain groups, that is, they can only take the effect of body weight and visceral fat reduction on overweight or obese groups.

Experiment 3: Preparation of the Pharmaceutical Compositions of the Present Invention Experiment 3-1: Preparation of Curcuminoid Simple Pharmaceutical Composition (a) a first weight of a curcuminoid or curcuminoids and a solvent were mixed, and stirred at 150 to 500 rpm at room temperature until curcumin dissolved completely;
(b) A second weight of a pharmaceutically acceptable surfactant was added, and stirred well at 100 to 300 rpm to volatilize the solvent, wherein, the hydrophilic-lipophilic balance value (HLB value) of the surfactant was greater than 10; and
(c) After the solvent volatilized completely, a third weight of a pharmaceutically acceptable aqueous solution was slowly added to obtain drug-containing micelles; and
(d) The mixture was filtered through a 0.2 μm filter membrane, and the filtrate comprising drug-containing micelles was stored in dark and refrigeration;
Wherein, in step (c), the drug-containing micelle was a microstructure formed from the surfactant, and the curcuminoid or curcuminoids was/were encapsulated in the drug-containing micelle; and the third weight was greater than or equal to 0 g.

Preferably, the operating procedure of step (c) is: after the solvent volatilizing completely, slowly adding the third weight of the pharmaceutically acceptable aqueous solution, and mixing well to form drug-containing micelles.

Preferably, in step (a), the boiling point of the solvent is lower than that of pure water.

Preferably, in step (a), the solvent is a hydrophilic solvent.
Preferably, the hydrophilic solvent is at least one of methanol, ethanol, acetone, and other hydrophilic solvents, or a combination thereof.

Preferably, the solvent in step (a) is a lipophilic (hydrophobic) solvent.

Preferably, the lipophilic (hydrophobic) solvent is at least one of ether, benzene, chloroform, ethyl acetate, dichloromethane, hexane, and other lipophilic (hydrophobic) solvents, or a combination thereof.

Preferably, in step (b), the surfactant is a non-ionic surfactant.

Preferably, the non-ionic surfactant is at least one of polysorbate 80 (Tween 80), 2-hydroxyethyl 12-hydroxyoctadecanoate (solutol HS 15), polyoxyethylene castor oil derivatives, and other non-ionic surfactants, or a combination thereof.

Preferably, the polyoxyethylene castor oil derivative is at least one of Kolliphor ELP (also known as Cremophor ELP), cremophor RH 40, and other polyoxyethylene castor oil derivatives, or a combination thereof.

Preferably, in steps (a) and (b), the weight ratio of the curcuminoid or curcuminoids of the first weight to the surfactant of the second weight is 1:5 to 1:500.

Preferably, in steps (a) and (b), the weight ratio of the curcumin of the first weight to the surfactant of the second weight is 1:20 to 1:150.

Preferably, in steps (a) and (c), the weight ratio of the curcuminoid or curcuminoids of the first weight to the pharmaceutically acceptable aqueous solution of the third weight is 1:400 to 3:50.

Preferably, in step (c), the pharmaceutically acceptable aqueous solution is water for injection, aqueous solution for injection, or normal saline.

Preferably, in step (c), the pharmaceutically acceptable aqueous solution comprises a local anesthetic.

Preferably, in step (c), the pharmaceutically acceptable aqueous solution comprises an antioxidant.

Experiment 3-2: Preparation of Curcuminoid-Other Lipophilic Drug Complex Pharmaceutical Composition The present invention provides a first preparation method for preparing a curcuminoid-other lipophilic drug complex pharmaceutical composition, and the curcuminoid-other lipophilic drug complex pharmaceutical composition comprises drug-containing micelles and the second lipophilic drug-containing micelles. The procedure of the first preparation to prepare the curcuminoid-other lipophilic drug complex pharmaceutical composition is as follows:
(A) Steps of preparing drug-containing micellar subassembly, to prepare a drug-containing micellar subassembly;
(B) Steps of preparing a second lipophilic drug-containing micellar subassembly, to prepare a second lipophilic drug-containing micellar subassembly; and
(C) Mixing the drug-containing micellar subassembly with the second lipophilic drug-containing micellar subassembly, to prepare the curcuminoid-other lipophilic drug complex pharmaceutical composition;
wherein, the step (A) to prepare the drug-containing micellar subassembly comprises the following steps (a2) to (d2):
(a2) A curcuminoid or curcuminoids and a first solvent are mixed, and stirred at 150 to 500 rpm at room temperature until the curcuminoid or curcuminoids dissolves completely;
(b2) A pharmaceutically acceptable first surfactant is added, and stirred well at 100 to 300 rpm to volatilize the first solvent, wherein, the hydrophilic-lipophilic balance value (HLB value) of the first surfactant is greater than 10;
(c2) After the first solvent volatilizing completely, the drug-containing micelles are obtained; and
(d2) The mixture is filtered through a 0.2 μm filter membrane, and the filtrate is the drug-containing micellar subassembly comprising drug-containing micelles;

and, the step (B) to prepare the second lipophilic drug-containing micellar subassembly comprised the following steps (a3) to (d3):

(a3) A second lipophilic drug and a second solvent are mixed, and stirred at 200 to 500 rpm at room temperature until the second lipophilic drug dissolved completely;

(b3) A pharmaceutically acceptable second surfactant is added, and stirred well at 100 to 300 rpm to volatilize the second solvent, wherein the hydrophilic-lipophilic balance value (HLB value) of the second surfactant is greater than 10;

(c3) After the second solvent volatilizes completely, the second lipophilic drug-containing micelles are obtained; and (d3) The mixture is filtrated through a 0.2 μm filter membrane, and the filtrate is the second lipophilic drug-containing micellar subassembly comprising the second lipophilic drug-containing micelles.

Wherein, in step (c2), the drug-containing micelle is a microstructure formed from the first surfactant, and the curcuminoid or curcuminoids is/are encapsulated in the drug-containing micelle. In step (c3), the second lipophilic drug-containing micelle is a microstructure formed from the second surfactant, and the second lipophilic drug is encapsulated in the second lipophilic drug-containing micelle.

Preferably, the operating procedure of step (c2) is: After the first solvent volatilizing completely, slowly adding a pharmaceutically acceptable aqueous solution and mixing well to form drug-containing micelles.

Preferably, the operating procedure of step (c3) is: After the second solvent volatilizing completely, slowly adding a pharmaceutically acceptable aqueous solution and mixing well to form the second lipophilic drug-containing micelles.

Preferably, the second lipophilic drug is at least one of quercetin, synephrine, puerarin, resveratrol, and other lipophilic drug except curcumin, or a combination thereof.

Preferably, in step (a2) and/or step (a3), the boiling point(s) of the first solvent and/or the second solvent are/is lower than the boiling point of pure water.

Preferably, in step (a2) and/or step (a3), the first solvent and/or the second solvent are/is a hydrophilic solvent.

Preferably, the hydrophilic solvent is at least one of methanol, ethanol, acetone, and other hydrophilic solvents, or a combination thereof.

Preferably, in step (a2) and/or step (a3), the first solvent and/or the second solvent are/is a lipophilic solvent.

Preferably, the lipophilic (hydrophobic) solvent is at least one of ether, benzene, chloroform, ethyl acetate, dichloromethane, hexane, and other lipophilic (hydrophobic) solvents, or a combination thereof.

Preferably, in step (b2) and/or (b3), the first surfactant and/or the second surfactant are/is a non-ionic surfactant.

Preferably, the non-ionic surfactant is at least one of polysorbate 80 (Tween 80), 2-hydroxyethyl 12-hydroxyoctadecanoate (solutol HS 15), polyoxyethylene castor oil derivatives, and other non-ionic surfactants, or a combination thereof.

Preferably, the polyoxyethylene castor oil derivative is at least one of Kolliphor ELP (also known as Cremophor ELP), cremophor RH 40, and other polyoxyethylene castor oil derivatives, or a combination thereof.

Preferably, the weight ratio of the curcuminoid or curcuminoids to the second lipophilic drug is 30:1 to 1:10.

Preferably, in steps (a2) and (b2), the weight ratio of the curcuminoid or curcuminoids and the first surfactant is 1:4 to 1:500.

Preferably, in steps (a3) and (b3), the weight ratio of the second lipophilic drug to the second surfactant is 1:4 to 1:500.

Preferably, in step (c2) and/or (c3), the pharmaceutically acceptable aqueous solution is water for injection, aqueous solution for injection, or normal saline.

Preferably, in step (c2) and/or (c3), the pharmaceutically acceptable aqueous solution comprises a local anesthetic.

Preferably, the local anesthetic is at least one of amides, para-aminobenzoic acid esters, and amino ethers, or a combination thereof.

Preferably, the amides are at least one of dibucaine, lidocaine, mepivacaine HCl, bupivacine HCl, pyrrocaine HCl, Prilocaine HCl, digammacaine, and oxethazaine, or a combination thereof.

Preferably, the para-aminobenzoic acid esters are at least one of butacaine, dimethocaine, and tutocaine, or a combination thereof.

Preferably, the amino ethers are at least one of quinisocaine and pramocaine, or a combination thereof.

Preferably, in step (c2) and/or (c3), the pharmaceutically acceptable aqueous solution comprises an antioxidant.

Preferably, the antioxidant is at least one of beta-carotene, lutein, lycopene, bilirubin, vitamin A, vitamin C (ascorbic acid), vitamin E, uric acid, nitric oxide, nitroxide, pyruvate, catalase, superoxide dismutase, glutathione peroxidases, N-acetyl cysteine, and naringenin, or a combination thereof.

The present invention provides a second preparation method of the curcuminoid-other lipophilic drug complex pharmaceutical composition, and the second preparation method of the curcuminoid-other lipophilic drug complex pharmaceutical composition is more concise than the first preparation method of the curcuminoid-other lipophilic drug complex pharmaceutical composition; and the procedure of the second preparation for the curcuminoid-other lipophilic drug complex pharmaceutical composition is as follows:

(a4) A curcuminoid or curcuminoids, the second lipophilic drug, and a solvent are mixed, and stirred at 200 to 500 rpm until the curcuminoid or curcuminoids dissolves completely;

(b4) A pharmaceutically acceptable surfactant is added and stirred well at 100 to 300 rpm to volatilize the solvent, wherein, the hydrophilic-lipophilic balance value (HLB value) of the surfactant is greater than 10;

(c4) Once the solvent volatilizes completely, a pharmaceutically acceptable aqueous solution is slowly added and mixed well to form drug-containing micelles and the second lipophilic drug-containing micelles; and (d4) The mixture is filtrated through a 0.2 μm filter membrane, and the filtrate comprising the drug-containing micelles and the second lipophilic drug-containing micelles is stored in dark and refrigeration.

The types and ranges of the solvents, the surfactants, the pharmaceutically acceptable aqueous solutions, and the second lipophilic drugs used in the second preparation method for the curcuminoid-other lipophilic drug complex pharmaceutical composition are the same as those used in the first preparation method of the curcuminoid-other lipophilic drug complex pharmaceutical composition. Additionally, the ranges of relative ratios of the ingredients used in the second preparation method of the curcuminoid-other lipophilic drug complex pharmaceutical composition are the same as those of the first preparation method of the curcuminoid-other lipophilic drug complex pharmaceutical composition.

Preferably, the pharmaceutically acceptable aqueous solutions comprise a local aesthetic and/or an antioxidant.

Preferably, the types and ranges of the local anesthetic and/or the antioxidant of the second preparation method of the curcuminoid-other lipophilic drug complex pharmaceutical composition are the same as those used in the first preparation method of the curcuminoid-other lipophilic drug complex pharmaceutical composition.

Experiment 3-3: Preparation of Curcuminoid-Water Soluble Drug Complex Pharmaceutical Composition (a5) A curcuminoid or curcuminoids and a solvent were mixed and stirred at 150 to 500 rpm at room temperature until the curcuminoid or curcuminoids dissolved completely;
(b5) A pharmaceutically acceptable surfactant was added and stirred well at 100 to 300 rpm to volatilize the solvent, wherein, the hydrophilic-lipophilic balance value (HLB value) of the surfactant was greater than 10;
(c5) After the solvent volatilized completely, a first pharmaceutically acceptable aqueous solution was slowly added and stirred well at 100 to 300 rpm to form drug-containing micelles; and
(d5) The mixture was filtrated through a 0.2 μm filter membrane, and the filtrate comprising drug-containing micelles was stored in dark and refrigeration;
wherein, the first pharmaceutically acceptable aqueous solution comprised a water soluble drug.

Preferably, the first pharmaceutical acceptable aqueous solution comprises a local aesthetic.

Preferably, the local anesthetic is at least one of amides, para-aminobenzoic acid esters, and amino ethers, or a combination thereof.

Preferably, the amides are at least one of dibucaine, lidocaine, mepivacaine HCl, bupivacine HCl, pyrrocaine HCl, prilocaine HCl, digammacaine, and oxethazaine, or a combination thereof.

Preferably, the para-aminobenzoic acid esters are at least one of butacaine, dimethocaine, and tutocaine, or a combination thereof.

Preferably, the amino ethers are at least one of quinisocaine and pramocaine, or a combination thereof.

Preferably, the first pharmaceutically acceptable aqueous solution comprises an antioxidant.

Preferably, the antioxidant is at least one of beta-carotene, lutein, lycopene, bilirubin, vitamin A, vitamin C (ascorbic acid), vitamin E, uric acid, nitric oxide, nitroxide, pyruvate, catalase, superoxide dismutase, glutathione peroxidases, N-acetyl cysteine, and naringenin, or a combination thereof.

Preferably, in step (a5), the boiling point of the solvent is lower than that of pure water.

Preferably, in step (a5), the solvent is a hydrophilic solvent.

Preferably, the hydrophilic solvent is at least one of methanol, ethanol, acetone, and other hydrophilic solvents, or a combination thereof.

Preferably, the solvent in step (a5) is a lipophilic (hydrophobic) solvent.

Preferably, the lipophilic (hydrophobic) solvent is at least one of ether, benzene, chloroform, ethyl acetate, dichloromethane, hexane, and other lipophilic (hydrophobic) solvents, or a combination thereof.

Preferably, in step (b5), the surfactant is a non-ionic surfactant.

Preferably, the non-ionic surfactant is at least one of polysorbate 80 (Tween 80), 2-hydroxyethyl 12-hydroxyoctadecanoate (solutol HS 15), polyoxyethylene castor oil derivatives, and other non-ionic surfactants, or a combination thereof.

Preferably, the polyoxyethylene castor oil derivative is at least one of Kolliphor ELP (also known as Cremophor ELP), Cremophor RH 40, and other polyoxyethylene castor oil derivatives, or a combination thereof.

Preferably, between steps (c5) and (d5), it further comprises the steps of: (c51) adding a second pharmaceutically acceptable aqueous solution and mixing well to completely dissolve the second pharmaceutically acceptable aqueous solution.

Preferably, the hydrophilic drug is dissolved in the first pharmaceutically acceptable aqueous solution, the drug-containing micelle is a microstructure formed by the surfactant, and the curcuminoid or curcuminoids is/are encapsulated in the drug-containing micelle.

Preferably, the water soluble drug in the first pharmaceutically acceptable aqueous solution is at least one of green tea extract, epigallocatechin gallate, epicatechin, epicatechin gallate, epigallocatechin, gallocatechin gallate, gallocatechin, catechin gallate, catechin, caffeine, carnitine, L-carnitine, synephrine, chlorogenic acid, and other water soluble drugs, or a combination thereof.

Preferably, in steps (a5) and (c5), the weight ratio of the curcuminoid or curcuminoids to the water soluble drug is 30:1 to 1:10.

Preferably, in steps (a5) to (c5), based on 1 weight unit defined as the total weight of the curcuminoid or curcuminoids and the water soluble drug, the weight of the surfactant is 0.24 to 70 weight units; or, the weight ratio of the total weight of the curcuminoid or curcuminoids and the water soluble drug to the surfactant is 4:1 to 1:70.

Preferably, in steps (a5), (c5), and (c51), based on 1 weight unit defined as the total weight of the curcuminoid or curcuminoids and the water soluble drug, the total weight of the first pharmaceutically acceptable aqueous solution and the second pharmaceutically acceptable aqueous solution is 16 to 400 weight units.

Preferably, in steps (c5) and (c51), the first pharmaceutically acceptable aqueous solution and the second pharmaceutically acceptable aqueous solution are water for injection, aqueous solution for injection, or normal saline.

Experiment 4: Determination of the Quality of Pharmaceutical Compositions

Experiment 4-1: Composition Analysis

The pharmaceutical composition was allowed to stand for at least 20 minutes. If the composition did not separate into layers, it was further analyzed by a particle size analyzer.

Whether the pharmaceutical composition included micelles was determined by a particle size analyzer. If the particle diameter of the pharmaceutical composition, after being analyzed by a particle size analyzer, was smaller than 250 nm, the solution of the pharmaceutical composition was deemed clear and transparent when observed by the naked eye, and the light beam could be observed when the solution of the pharmaceutical composition was shined by a laser, then it indicated that the pharmaceutical composition comprised micelles.

If micelles are present in the pharmaceutical composition, the prepared pharmaceutical composition is the pharmaceutical composition for reducing body weight and body fat in the present invention.

Preferably, if the pharmaceutical composition does not separate into layers and does not contain precipitates after being let stand, the prepared pharmaceutical composition is the preferable pharmaceutical composition of the present invention.

Experiment 4-2: Determination of the Stability of Pharmaceutical Compositions by Analyzing the Distribution of Particle Diameters The distribution of particle diameters and the polydispersity index (PDI) were determined using a particle size analyzer (purchased from Malvern). If PDI is less than 0.4, it indicates that the stability of pharmaceutical composition is good, that is, the micelles in the pharmaceutical composition can exist stably.

Experiment 4-3: Determination of the Stability of Pharmaceutical Compositions by an Accelerated Stability Test The storage condition of the pharmaceutical composition of the present invention is 2 to 8° C. In order to test the stability of the pharmaceutical compositions, the inventor placed the pharmaceutical compositions in an environment of relatively high temperature and relatively high humidity (temperature 25° C.±2° C., relative humidity 60%±5%) for an accelerated stability test, and how long the micelles in the pharmaceutical composition was able to stably exist in a condition of relatively high temperature was observed for reckoning the shelf life of the pharmaceutical composition at 2 to 8° C. based on the accelerated stability test equation as detailed below.

If the pharmaceutical composition has a shelf life of n months at a condition of 25° C., then the shelf life of the pharmaceutical composition at a condition of 5° C. is $2^{((25-5)/10)}$ folds of n months. That is, the shelf life of the pharmaceutical composition at a condition of 5° C. is $2^2$ folds of n months, that is, 4 folds.

For example, if the shelf life of the pharmaceutical composition is 6 months at a condition of 25° C., then the shelf life of the pharmaceutical composition at a condition of 5° C. is 24 months (6 months×4 folds=24 months.)

Preferably, the pharmaceutical composition maintains at a state without precipitations for at least 24 hours when it is subjected to accelerated stability test at a condition of temperature of 25° C.±2° C., relatively humidity of 60%±5%, and in the absence of direct light.

Preferably, the pharmaceutical composition maintains at a state without precipitations for at least 6 months when it is subjected to accelerated stability test at a condition of temperature of 25° C.±2° C., relatively humidity of 60%±5%, and in the absence of direct light.

Preferably, the pharmaceutical composition maintains at a state without precipitations for at least 24 months at a condition of temperature of 2 to 8° C.

Experiment 5: Maximum Drug Load of Drug-Containing Micelles Formed from Various Non-Ionic Surfactants Because the maximum drug load of drug-containing micelles directly affects injection volume, it greatly influences the volume of drug, side effects, and the burden that have to be tolerated by localized subcutaneous location in a single administration. Thus, in this experiment, the maximum drug load of curcumin within drug-containing micelles, in per unit of pharmaceutical composition, formed from various non-ionic surfactants was investigated, to determine which non-ionic surfactant was the best excipient for preparing the pharmaceutical compositions of the present invention.

Four non-ionic surfactants were selected for this experiment. The four non-ionic surfactants were Kolliphor ELP (also known as Cremophor ELP, abbreviated as ELP), Kolliphor HS-15 (HS-15), Cremophor RH 40 (abbreviated as RH 40), and polysorbate 80 (also known as Tween 80).

There were 4 groups, i.e. an ELP group, an HS-15 group, an RH40 group, and a Tween 80 group, in the experiment.

Experimental Procedure (a') 2.0 g (an example of the first weight) of curcumin was mixed with 300 to 500 mL of dichloromethane, and stirred at 150 to 500 rpm at room temperature until curcumin dissolved completely.

(b') 18.0 g (an example of the second weight) of one of the non-ionic surfactants mentioned above was added to the solution, and stirred at 100 to 300 rpm to volatilize dichloromethane; and (c') A composition of 20 g in total was obtained after the solvent volatilized completely; 2 g of the composition was weighed out, and 8 g (an example of the third weight) of normal saline for injection was added slowly and mixed well to obtain a composition to be tested. The concentration of curcumin in the composition to be tested was 20 mg/g, and the concentration of the non-ionic surfactant was 18%.

The compositions to be tested from the ELP group, the HS-15 group, the RH40 group, and the Tween 80 group were allowed to stand for at least 20 minutes to observe if separation occurred. If separation occurs, it indicates that the concentration of curcumin is too high and thus causes the micelles in the composition to be tested to burst, that is, such non-ionic surfactant cannot be used to prepare the pharmaceutical compositions of the present invention in which curcumin concentration is 20 mg/g.

The experimental results showed that the compositions to be tested in the HS-15 group and the RH40 group separated into layers, and only the compositions to be tested from the ELP group and the Tween 80 group did not separate. Therefore, the maximum drug load of curcumin within the drug-containing micelles formed from HS-15 and RH40 in per gram of the pharmaceutical compositions are both smaller than 20 mg/g. The maximum drug load of curcumin within the drug-containing micelles formed from ELP and Tween 80 in per gram of the pharmaceutical compositions is greater than or equal to 20 mg/g.

However, because Tween 80 is toxic, according to various national pharmacopoeias, the injection concentration of Tween 80 is limited to be less than 0.4% to avoid adverse effects or toxicity. Thus, the maximum drug load of curcumin within the drug-containing micelles formed from Tween 80 in per gram of the pharmaceutical compositions should be 0.44 mg/g as an upper limit. (Calculation: 20 mg/g×(0.4%/18%)=0.44 mg/g.)

In order to determine the maximum drug load of ELP, the inventor further performed experiments and determined that the maximum drug load of ELP in per gram of pharmaceutical composition is greater than or equal to 167 mg of curcumin.

The results above indicated that ELP is the best excipient to prepare the pharmaceutical compositions of the present invention. The maximum drug load of curcumin in drug-containing micelles, formed from ELP, can reach 167 mg in per gram of the pharmaceutical compositions, while the maximum drug load of curcumin in drug-containing micelles, formed from other non-ionic surfactants, in per gram of the pharmaceutical compositions is less than 20 mg/g (please refer to Table 1).

In order to determine which of the drug-comprising micelles formed from non-ionic surfactants HS-15 and RH40 has the lowest upper limit of drug load of curcumin in per unit of pharmaceutical composition, the inventor further used those non-ionic surfactants to prepare the pharmaceutical compositions of the present invention wherein the concentration of curcumin is 10 mg/g. The results showed that ELP, HS-15, RH40, and Tween 80 can all be used to prepare the pharmaceutical compositions of the present invention with 10 mg/g of curcumin, and the pharmaceutical compositions of the present invention with 10 mg/g of curcumin were clear without separation, and the measured particle diameters were 15.95±0.24 nm, 88.23±116.06 nm, 21.63±9.34 nm, 11.37±0.13 nm, respectively, and the PDI values were 0.32±0.02, 0.48±0.27, 0.26±0.09, 0.33±0.04, respectively.

Among them, when HS-15 was used to prepare the pharmaceutical composition of the present invention with a curcumin concentration of 10 mg/g, the PDI value of the prepared pharmaceutical composition was greater than 0.4, which does not meet the definition of the present invention on the micelles in the pharmaceutical composition about possession of stability. Therefore, among the non-ionic surfactants selected for this experiment, HS-15 has the lowest upper limit of drug load (please refer to Table 1).

TABLE 1

Maximum drug load of drug-containing micelles formed from various non-ionic surfactants

| Group | Maximum drug load of the micelles for curcumin in pharmaceutical composition per gram (mg) | Maximum tolerated dosage of micellar drug load to the body in per gram of pharmaceutical composition (mg) |
| --- | --- | --- |
| ELP group | ≥167 | ≥167 |
| HS-15 group | <10 | <10 |
| RH40 group | <20; ≥10 | <20; ≥10 |
| Tween 80 group | ≥20 | 0.44 |

Experiment 6: Preparation of Pharmaceutical Compositions with Kolliphor ELP (ELP)

In order to determine both of the appropriate ratio of curcumin to Kolliphor ELP (ELP) and the maximum drug load when preparing the pharmaceutical compositions in the present invention with ELP, various ratios of curcumin to Kolliphor ELP (also known as Cremophor ELP, abbreviated as ELP) were used in this experiment to prepare a series of pharmaceutical compositions of the present invention, and the stability analysis thereof were performed.

There were 9 groups in this experiment, that is, the $1^{st}$ to the $9^{th}$ group. The preparation method of pharmaceutical composition in each group was substantially the same as the experimental procedure in Experiment 5, and only the weight of curcumin (the first weight in step (a')), the weight of ELP (the second weight in step (b')), and the weight of normal saline for injection (the third weight in step (c')) were different. In this experiment, the guideline of adding of the weight of curcumin (the first weight), the weight of ELP (the second weight), and the weight of normal saline for injection (the third weight) are as shown in Table 2.

TABLE 2

A sample preparation chart for preparing pharmaceutical compositions with ELP

| Group | Ratio of curcumin to ELP (weight ratio) | Final concentration of curcumin in the pharmaceutical composition (mg/g) |
| --- | --- | --- |
| $1^{st}$ | 1:4 | 200 |
| $2^{nd}$ | 1:5 | 167 |
| $3^{rd}$ | 1:8 | 111 |
| $4^{th}$ | 1:10 | 91 |
| $5^{th}$ | 1:20 | 47.62 |
| $6^{th}$ | 1:40 | 7.5 |
| $7^{th}$ | 1:100 | 3 |
| $8^{th}$ | 1:150 | 2 |
| $9^{th}$ | 1:500 | 0.5 |

In this experiment, the ratios of curcumin to ELP (weight ratio) in the first group to the ninth group were 1:4, 1:5, 1:8, 1:10, 1:20, 1:40, 1:100, 1:150, and 1:500, respectively, and the final concentrations of curcumin in the pharmaceutical compositions prepared in the first to the ninth group were 200 mg/g, 167 mg/g, 111 mg/g, 91 mg/g, 47.62 mg/g, 7.5 mg/g, 3 mg/g, 2 mg/g, and 0.5 mg/g, respectively. That is, in the preparation method of pharmaceutical composition in the first to the ninth group, the weight ratios of curcumin in step (a') to ELP in step (b') (the ratios of the first weight to the second weight) were 1:4, 1:5, 1:8, 1:10, 1:20, 1:40, 1:100, 1:150, and 1:500, respectively, and that after adding the third weight of normal saline for injection in step (c'), the final concentrations of curcumin in the prepared pharmaceutical compositions were 200 mg/g, 167 mg/g, 111 mg/g, 91 mg/g, 47.62 mg/g, 7.5 mg/g, 3 mg/g, 2 mg/g, and 0.5 mg/g, respectively. Wherein, when the final concentration of drug was presented as mg/g, it indicated the amount of milligrams of curcumin per gram of pharmaceutical composition.

A particle size analyzer was utilized to determine if micelles were present in the pharmaceutical compositions, and the particle diameter of the micelles was measured.

To assess the stability of the pharmaceutical compositions, the distribution of particle diameters and the polydispersity index (PDI) were measured by a particle size analyzer. The curcumin content in the micelles was analyzed by high performance liquid chromatography (HPLC; e.g., HPLC-UV) and defined as the "initial drug content".

The pharmaceutical compositions were subjected to accelerated stability test to observe if separation occurred when the pharmaceutical compositions were stored at high temperature storage condition (25±2° C.) for 3 months. The drug content in the micelles was analyzed by high performance liquid chromatography (HPLC; e.g., HPLC-UV), and defined as the "drug content after accelerated stability test". The "percentage of drug content" was calculated by dividing the "drug content after accelerated stability test" by the "initial drug content". If the percentage of drug content is greater than or equal to 95%, it indicates that the stability of the pharmaceutical composition is excellent.

Please refer to Table 3. Table 3 is the stability analysis result of the pharmaceutical compositions. Table 3 shows the presence of micelles in the second to the ninth pharmaceutical compositions. Therefore, pharmaceutical compositions prepared with curcumin to ELP ratios of 1:5 to 1:500 are all pharmaceutical compositions for reducing body weight and visceral fat in the present invention.

TABLE 3

Stability analysis of the pharmaceutical compositions

| Group | Ratio of curcumin to ELP (weight ratio) | Micelle particle diameter (nm) | PDI | Appearance after accelerated stability test | Percent of drug content after accelerated stability test (%) |
|---|---|---|---|---|---|
| 1st | 1:4 | 772.5 ± 198.92 | 0.79 ± 0.36 | | |
| 2nd | 1:5 | 153.97 ± 40.17 | 0.41 ± 0.13 | | |
| 3rd | 1:8 | 13.17 ± 0.21 | 0.2 ± 0.02 | | |
| 4th | 1:10 | 12.47 ± 0.23 | 0.17 ± 0.01 | | |
| 5th | 1:20 | 12.57 ± 0.12 | 0.137 ± 0.03 | Clear without separation | 103.82 ± 2.07 |
| 6th | 1:40 | 11.59 ± 0.27 | 0.174 ± 0.0 | Clear without separation | 100.78 ± 0.51 |
| 7th | 1:100 | 12.26 ± 0.12 | 0.096 ± 0.07 | Clear without separation | 100.62 ± 0.21 |
| 8th | 1:150 | 12.93 ± 0.29 | 0.197 ± 0.02 | Clear without separation | 102.45 ± 0.05 |
| 9th | 1:500 | 12.66 ± 0.14 | 0.16 ± 0.01 | | |

In the table above, blank cells indicate that the contents were not analyzed.

In terms of stability, when the ratios of curcumin to ELP were 1:4 and 1:5, both PDI were greater than 0.4. When the ratios of curcumin to ELP were 1:8 to 1:500, each PDI was smaller than 0.4. Thus, in order to prepare the pharmaceutical composition with better stability, the ratio of curcumin to ELP should be less than one-fifth (1/5). That is, in order to prepare the pharmaceutical composition with better stability, based on 1 weight unit defined as the weight of curcumin, the weight of ELP should be greater than 5 weight units. Preferably, based on 1 weight unit defined as the weight of curcumin, the weight of ELP is 8 to 500 weight units. Preferably, based on 1 weight unit defined as the weight of curcumin, the weight of ELP is 20 to 150 weight units.

Based on the data in Table 3, when the pharmaceutical compositions in the fifth to the eighth group were stored at 25° C. for 3 months, the percentage of curcumin drug content in every sample was greater than 95% and did not show a significant trend of decrease comparing to the initial drug content. This result indicates that the pharmaceutical compositions have excellent stability, and based on the equation of accelerated stability test, the pharmaceutical compositions can be stored at 2 to 8° C. in refrigeration for at least 24 months.

Experiment 7: The Effect of Drug-Containing Micelle Concentration on the Stability of Pharmaceutical Composition and the Efficacy of Weight Reduction According to the context of invention in Taiwan patent application number 105127451 of the inventor, the inventor believes that the concentration of drug-containing micelles could affect the stability, efficacy of weight reduction, and safety of the pharmaceutical composition in the present invention. Thus, a series of pharmaceutical composition having different drug-containing micelle concentrations was prepared with the same preparation method, and determine the stability, efficacy of weight reduction, and safety measurements (whether ulcer would occur at the administration site).

Experiment 7-1: Preparation of Pharmaceutical Composition

There were 12 tubes of pharmaceutical composition in this experiment, that is, the first to twelfth tube. The preparation method of the first tube pharmaceutical composition was:

18 mg (an example of the first weight) of curcumin was mixed with 80 to 140 ml of dichloromethane, and stirred at 150 to 500 rpm at room temperature until dissolved completely. 90 g (an example of the second weight) of Kolliphor ELP (also known as Cremophor ELP) was added to the solution, and stirred at 100 to 300 rpm to volatilize dichloromethane. Normal saline for injection was slowly added after the dichloromethane volatilized completely to make the final volume to reach 180 ml, to form drug-comprising micelles to obtain the first tube pharmaceutical composition for this experiment. Curcumin precipitation did not happen to the pharmaceutical composition that is just prepared by this method, and the specific gravity of pharmaceutical composition was about 1 mg/mL; therefore, in the first tube pharmaceutical composition, the total concentration of curcumin encapsulated in drug-comprising micelles was 0.1 mg/mL (18 mg÷180 g=0.1 mg/g)

The preparation method of the second to twelfth tube pharmaceutical composition was about the same with the preparation method of the first tube pharmaceutical composition, with the exception of the difference in the weight of curcumin (first weight) and the weight of the ELP (second weight); however, the weight ratio of curcumin to Kolliphor ELP was also 1:5. The guideline of adding of curcumin weight (the first weight) and ELP weight (the second weight) when preparing the first to twelfth pharmaceutical composition are as shown in Table 4.

TABLE 4

A sample preparation chart for preparing pharmaceutical compositions with ELP

| Tube | Weight of curcumin in pharmaceutical composition (g) | Weight of ELP in pharmaceutical composition (g) | Total concentration of curcumin encapsulated in drug-comprising micelles (mg/g) |
|---|---|---|---|
| $1^{st}$ | 0.018 | 0.09 | 0.1 |
| $2^{nd}$ | 0.045 | 0.225 | 0.25 |
| $3^{rd}$ | 0.072 | 0.36 | 0.4 |
| $4^{th}$ | 0.09 | 0.45 | 0.5 |
| $5^{th}$ | 0.36 | 1.8 | 2 |
| $6^{th}$ | 0.54 | 2.7 | 3 |
| $7^{th}$ | 1.35 | 6.75 | 7.5 |
| $8^{th}$ | 8.5716 | 42.858 | 47.62 |
| $9^{th}$ | 16.38 | 81.9 | 91 |
| $10^{th}$ | 19.98 | 99.9 | 111 |
| $11^{th}$ | 30.06 | 150.3 | 167 |
| $12^{th}$ | 31.5 | 157.5 | 175 |

Experiment 7-2: Stability Analysis of the Pharmaceutical Compositions

A particle size analyzer was utilized to determine if micelles were present in the pharmaceutical compositions, and the particle diameter of the micelles was measured.

To assess the stability of the pharmaceutical compositions, the distribution of particle diameters and the polydispersity index (PDI) were measured by a particle size analyzer. The curcumin content in the micelles was analyzed by high performance liquid chromatography (HPLC; e.g., HPLC-UV) and defined as the "initial drug content".

The pharmaceutical compositions were subjected to accelerated stability test to observe if separation occurred when the pharmaceutical compositions were stored at high temperature storage condition (25±2° C.) for 3 months. The drug content in the micelles was analyzed by high performance liquid chromatography (HPLC; e.g., HPLC-UV), and defined as the "drug content after accelerated stability test". The "percentage of drug content" was calculated by dividing the "drug content after accelerated stability test" by the "initial drug content". If the percentage of drug content is greater than or equal to 95%, it indicates that the stability of the pharmaceutical composition is excellent.

The results of stability analysis of the pharmaceutical compositions please refer to Table 5.

After the first to eleventh tube of drug-comprising pharmaceutical composition were analyzed by a particle size analyzer, the particle diameter measured was smaller than 250 nm and the PDI value was less than 0.4, the solution of the pharmaceutical composition was deemed clear and transparent, the solution did not separate and did not contain precipitates after being allow to stand, the light beam could be observed when the solution of the pharmaceutical composition is shined by a laser, and the pharmaceutical composition maintained at a state without precipitations for at least 24 hours when it is subjected to the conditions of temperature of 25° C.±2° C. and relatively humidity of 60%±5%. Therefore, when the total concentration of curcumin encapsulated in drug-containing micelles are in the range of 0.1 to 167 mg/g, the pharmaceutical composition possesses stability. However, the twelfth tube of drug-comprising pharmaceutical composition had a PDI value found to be greater than 0.4, after being analyzed by a particle size analyzer, Therefore, when the total concentration of curcumin encapsulated in drug-containing micelles is 175 mg/g, the pharmaceutical composition does not have stability.

Experiment 7-3: Weight Reduction Efficacy of the Pharmaceutical Composition

Six-week-old male Sprague-Dawley rats were used for the experiment. 52 rats were fed with normal diet for 1 week to allow weight to be 175 to 200 g, and then fed with high fat diet to be induced into an obese animal mode. The rats were divided into 13 groups, that is, the control group, the first group, the second group, the third group, the fourth group, the fifth group, the sixth group, the seventh group, the eighth group, the ninth group, the tenth group, the eleventh group, the twelfth group, with four rats per group, to make no statistical difference for the weight in each group of rats. Thereafter, subcutaneous injections were administered as follows.

The first to twelfth group: the first to twelfth group rats were administered with the first to twelfth tube pharmaceutical composition of Experiment 7-1 via subcutaneous injection, and the injection site was behind the ear on the back, above the scapula, or below the scapula of rats, respectively.

Control group: the control group rats were administered with normal saline for injection via subcutaneous injection, and the injection site was behind the ear on the back, above the scapula, or below the scapula of rats.

High-fat diet was consistently given during the experiment period, for a duration of 20 days and the rats were sacrificed with $CO_2$ on day 21. Whether if the condition of ulcer occurred on the administration site of the rats to be injected with the pharmaceutical composition was observed, and calculate the "relative total weight gain" and "relative visceral fat weight."

Please refer to Table 5 for weight reduction efficacy of the pharmaceutical composition.

TABLE 5

The results of weight reduction efficacy and drug-containing micelles stability of pharmaceutical composition in different concentrations

| Group | The total concentration of curcumin encapsulated in the drug-containing micelles (mg/g) | Weight reduction efficacy | micelles stability |
|---|---|---|---|
| $1^{st}$ | 0.1 | X | V |
| $2^{nd}$ | 0.25 | X | V |
| $3^{rd}$ | 0.4 | V | V |
| $4^{th}$ | 0.5 | V | V |
| $5^{th}$ | 2 | V | V |
| $6^{th}$ | 3 | V | V |
| $7^{th}$ | 7.5 | V | V |
| $8^{th}$ | 47.62 | V | V |
| $9^{th}$ | 91 | V | V |
| $10^{th}$ | 111 | V | V |
| $11^{th}$ | 167 | V | V |
| $12^{th}$ | 175 | V | X |

Experimental results indicated that, in comparison with the control group, the "relative total weight gain" and "relative visceral fat weight" of the first group rats had not decreased significantly (p>0.05), and the "relative total weight gain" and "relative visceral fat weight" of the second group rats did not decrease significantly (p>0.05), either. However, the "relative total weight gain" and "relative visceral fat weight" of the rats in the third to the twelfth group had all decreased significantly (p<0.05). Therefore, in the pharmaceutical composition, when the total concentration of curcumin encapsulated in drug-containing micelles are in the range of 0.4 to 200 mg/g, its effect on body weight and visceral fat reduction in rats can be achieved.

The results above indicated that, in the pharmaceutical composition, when the total concentration of curcumin encapsulated in drug-containing micelles is greater than or equal to 0.4 mg/g, its effect on body weight and visceral fat reduction in the rats can be achieved; on the other hand, when the total concentration of curcumin encapsulated in drug-containing micelles is less than or equal to 167 mg/g, the stability of the micelles can be maintained. Therefore, in the pharmaceutical composition in the present invention, when the total concentration of curcumin encapsulated in drug-containing micelles is in the range of 0.4 to 167 mg/g, both of the stability and effects on weight reduction can be achieved. Preferably, in the pharmaceutical composition of the present invention, the total concentration of curcumin encapsulated in drug-containing micelles is 0.4 to 111 mg/g.

Experiment 8: The Effects of Different Ratios of Curcumin-Green Tea Extraction Complex Pharmaceutical Composition on the Weight and the Visceral Fat Weight of Rats There were 12 tubes of the curcumin-green tea extract complex pharmaceutical composition in the present experiment, that is, the curcumin tube, green tea extract tube, the 1' to 4' tube, the 6' to 7' tube, the 9' tube, and the 11' to 13' tube. The preparation of each tube was substantially the same as the experimental procedure in Experiment 1; the only difference was the ratio of curcumin to green tea extract, and the concentration of Cremophor ELP was 15%. The ratio of curcumin to green tea extract shown in Table 6.

TABLE 6 the weight ratio and total concentration of curcumin and green tea extract in the curcumin-green tea extract complex pharmaceutical compositions

| Tube | The ratio of curcumin to green tea extract (weight ratio) | The total concentration of curcumin and green tea extract (mg/mL) |
| --- | --- | --- |
| Curcumin | 1:0 | 5 |
| Green tea extract | 0:1 | 5 |
| 1' | 50:1 | 5 |
| 2' | 30:1 | 5 |
| 3' | 10:1 | 5 |
| 4' | 7:1 | 5 |
| 6' | 4:1 | 5 |
| 7' | 1:1 | 5 |
| 9' | 1:4 | 5 |
| 11' | 1:10 | 5 |
| 12' | 1:20 | 5 |
| 13' | 3:2 | 5 |

Six-week-old male Sprague-Dawley rats were used for the experiment. 52 rats were fed with normal diet for three days to allow weight to be 175 to 200 g, and then fed with high fat diet for 21 days, to be induced into an obese animal mode and to increase body weight to 400 to 500 g. Afterwards, the rats were randomly assigned into 13 groups, that is, high-fat control group, curcumin group, green tea extract group, the OIG1 to OIG4 group, the OIG6 to OIG7 group, the OIG 9 group, and the OIG11 to OIG13 group, with four rats per group, for there to be no statistical difference for weight in each group of rats. Administration method of drugs was follows.

High-fat control group: the rats were administered with normal saline for injection via subcutaneous injection; and the administration sites were behind the ear on the back, above the scapula, or below the scapula of rats. One injection was administered each day on the day 1, day 3, day 5, day 7, day 9, and day 11 in the experiment, for a total of 6 injections, and the dosage per injection is 4 mL per kilogram of body weight (4 mL/kg).

Curcumin group, green tea extract group, the OIG1 to OIG4 group, the OIG6 to OIG7 group, the OIG9 group, and the OIG11 to OIG13 group: the pharmaceutical composition in the curcumin tube, the green tea extract group, the 1' to 4' tube, the 6' to 7' tube, the 9' tube, and 11' to 13' tube were administered to the rats in the curcumin group, the green tea extract group, the OIG1 to OIG4 group, the OIG6 to OIG7 group, the OIG9 group, and OIG11 to OIG13 group, respectively, and the administration sites were behind the ear on the back, above the scapula, or below the scapula of rats. One injection was administered per day on the day 1, day 3, day 5, day 7, day 9, day 11, for a total of 6 injections, and the dosage per injection was 4 ml per kilogram of body weight (4 mL/kg), to make the dosage per injection to be 20 mg of drugs per kilogram of body weight (the total concentration of curcumin and green tea extract administrated per kilogram is 4 mL/kg×5 mg/mL=20 mg/kg).

High-fat diet was given consistently during the experiment for 20 days, and the rat was sacrificed with $CO_2$, on day 21, and the "relative total weight gain" and "relative visceral fat weight" were calculated.

Figure 2A:
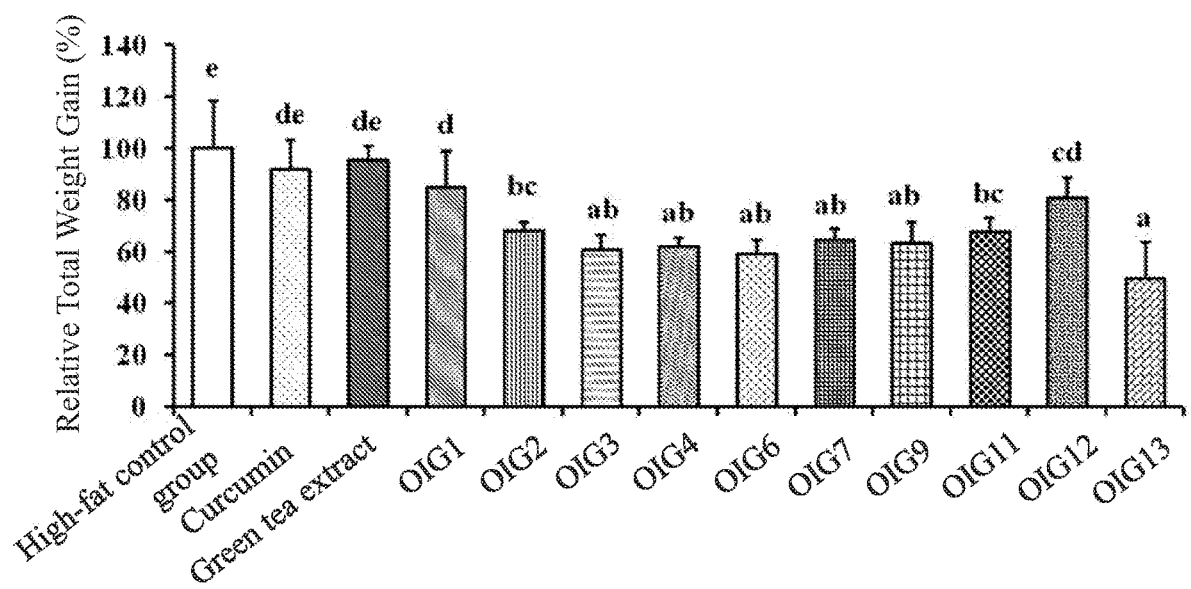
FIG. 2A: A bar graph showing the effect of the ratio of curcumin to green tea extract on the relative total weight gain of rats.

Results as shown in FIG. 2A indicate that, the relative total weight gains of rats in the high-fat control group is 100.0±18.5%, the relative total weight gain of rats in the curcumin group is 92.1±11.3%, the relative total weight gain of rats in the green tea extract group is 95.4±5.6%, the relative total weight gains of rats in the OIG1 to OIG4 group, the OIG6 to OIG7 group, the OIG9 group, and the OIG11 to OIG13 group are 85.1±13.6%, 68.4±3.1%, 61.0±5.6%, 62.3±3.3%, 59.3±5.4%, 64.4±4.8%, 63.5±8.1%, 67.7±5.3%, 80.8±7.9%, and 49.4±14.3%, respectively. Among them, in comparison with the high-fat control group, the total weight gain of rats in the curcumin group and the green tea extract group did not reduce significantly (p>0.05), indicating that if the rat is simply provided with curcumin or green tea extract, the weight of rat cannot be reduced significantly under the conditions of the present experiment (p>0.05). However, in comparison with high-fat diet control group, the relative total weight gain of rats in the OIG1 to OIG4 group, the OIG6 to OIG7 group, the OIG9 group, and the OIG11 to OIG13 group all had reduced significantly (p<0.05), indicating that when the ratio of curcumin to green tea extract is in the range of 50:1 to 1:20, the body weight of rat can be reduced significantly. Furthermore, in comparison with the curcumin group or the green tea extract group, the total weight gain of rats in the OIG2 to OIG4 group, the OIG6 to OIG7 group, the OIG9 group, the OIG11 group, and the OIG13 group all had been reduced significantly (p<0.05), indicating when the ratio of curcumin to green tea extract is in the range of 30:1 to 1:10, synergy is present. Preferably, when the ratio of curcumin to green tea extract is in the range of 10:1 to 1:4, preferred synergy is present.

Figure 2B:
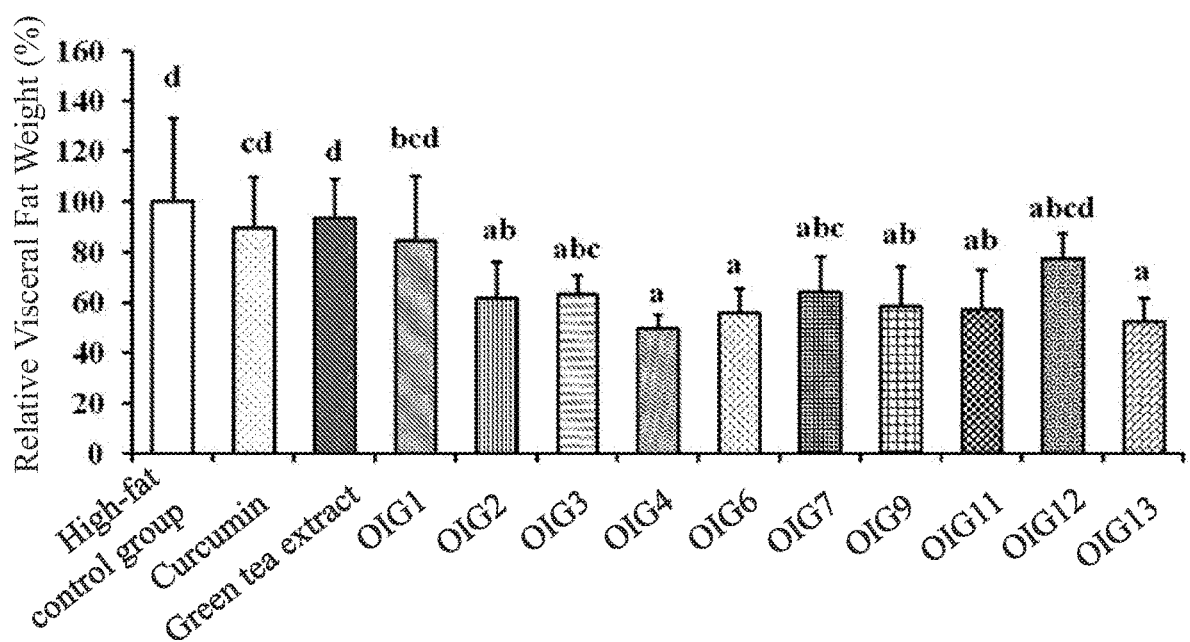
FIG. 2B: A bar graph showing the effect of the ratio of curcumin to green tea extract on the relative weight of visceral fat of rats.

Results as shown in FIG. 2B indicate that, the relative visceral fat weight of rats in the high-fat control group is 100.0±33.4%, the relative visceral fat weight of rats in the curcumin group is 89.7±19.9%, the relative visceral fat weight of rats in the green tea extract group is 93.7±15.2%, the relative visceral fat weights of rats in the OIG1 to OIG4 group, the OIG6 to OIG7 group, the OIG9 group, and the OIG11 to OIG13 group are 84.3±26.1%, 61.9±14.2%, 63.5±7.5%, 50.1±5.0%, 56.0±9.6%, 64.5±13.6%, 58.9±15.6%, 57.6±15.6%, 77.4±10.1%, and 52.8±9.1%, respectively. Among them, in comparison with the high-fat control group, the relative visceral fat weight of rats in the curcumin group and the green tea extract group had not been reduced significantly (p>0.05), indicating if curcumin or green tea extract is simply provided, the visceral fat in rats cannot be reduced significantly under the conditions of the present experiment (p>0.05). However, in comparison with rats of high-fat control group, the relative visceral fat weights of rats in the OIG2 to OIG4 group, the OIG6 to OIG7 group, the OIG9 group, and the OIG11 group, and the OIG13 group all reduced significantly (p<0.05), indicating when the ratio of curcumin to green tea extract is in the range of 30:1 to 1:10, visceral fat of rats can be reduced significantly. Furthermore, in comparison with the curcumin group or the green tea extract group, the weight of relative visceral fats of rats in the OIG2 group, the OIG4 group, the OIG6 group, the OIG9 group, the OIG11 group, and the OIG13 group all had reduced significantly (p<0.05), indicating when the ratio of curcumin to green tea extract is in the range of 30:1 to 1:10, synergy is present. Preferably, the ratio of curcumin to green tea extract is 7:1 to 1:1.

Experiment 9: Effects of Different Dosages of Curcumin-Green Tea Extract Complex Pharmaceutical Composition on the Body Weight and Visceral Fat Weight of Rats The preparation of curcumin-green tea extract complex pharmaceutical composition was the same as the procedure of that for the 13' tube in Experiment 8, that is, the ratio of curcumin to green tea extract was 3:2 and the concentration of Cremophor ELP was 15%.

Six-week-old male Sprague-Dawley rats were used for the experiment. 20 rats were fed with normal diet for three days to allow weight to be 175 to 200 g, and then the rats are assigned into 5 groups; that is normal control group, high-fat control group, low dosage group, medium dosage group, and high dosage group. Afterwards, the rats in the normal control group were fed with normal diet continuously for totally 21 days, and, at the same time, the rats in the high-fat control group, the low dosage group, the medium dosage group, and the high dosage group were fed with high-fat diet for 21 days, to be induced into an obese animal mode and allowed body weight to increase up to 400 to 450 g. Thereafter, subcutaneous injections were administered as follows.

Normal control group and High-fat control group: normal saline for injection was administered to the rats in the normal control group and the high-fat control group via subcutaneous injection, and the administration sites were behind the ear on the back, above the scapula, or below the scapula of rats. One injection per day was administered on the day 1, day 3, day 5, day 7, day 9, and day 11 in the experiment, for a total of 6 injections, and the dosage per injection is 8 mL per kilogram of body weight (8 mL/kg).

Low dosage group: curcumin-green tea extract complex pharmaceutical composition of the present experiment was administered to the rats via subcutaneous injection, and the administration sites were behind the ear on the back, above the scapula, or below the scapula of rats. One injection per day was administered on the day 1, day 3, day 5, day 7, day 9, and day 11 in the experiment, for a total of 6 injections, and the dosage per injection was 2 mL per kilogram of body weight (2 mL/kg), to make administration dosage per injection to be 6 mg of curcumin and 4 mg of green tea extract per kilogram of body weight.

Medium dosage group: The way and frequency of injection administrations were same as those for the low dosage group, with the only difference in injection dosage. The dosage per injection is 4 mL per kilogram of body weight (4 mL/kg), to make the administration dosage per injection to be 12 mg of curcumin and 8 mg of green tea extract per kilogram of body weight.

High dosage group: The way and frequency of injection administrations were same as those for the low dosage group, with the only difference in injection dosage. The dosage per injection was 8 mL per kilogram of body weight (8 mL/kg), to make administration dosage per injection to be 24 mg of curcumin and 16 mg of green tea extract per kilogram of body weight.

High fat diet was consistently given during the experiment period, for a duration of 20 days, the rats were sacrificed with $CO_2$ on day 21, and the "relative total weight gain" and "relative visceral fat weight" of rats in each group were calculated.

Figure 3A:
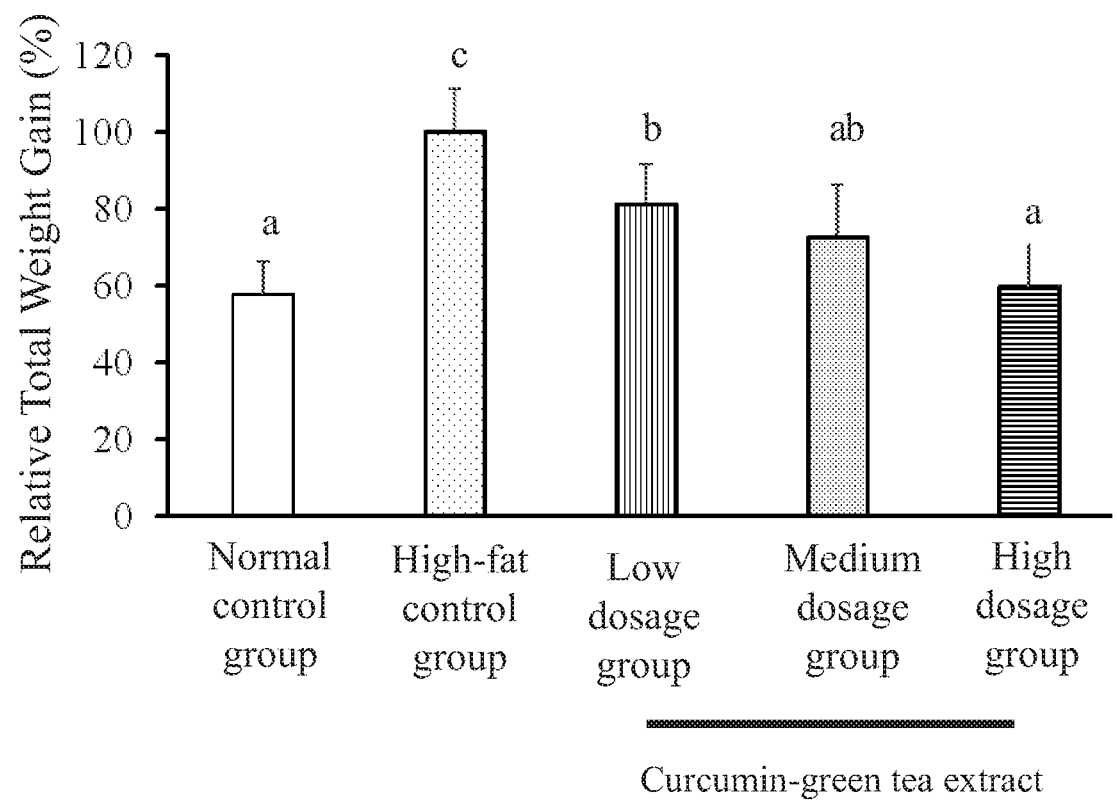
FIG. 3A: A bar graph showing the effect of the dosage of curcumin-green tea extract complex pharmaceutical composition on the relative total weight gain of rats.

Results as shown in FIG. 3A indicate that, the relative total weight gain of rats in the normal control group was 57.4±8.6%, the relative total weight gain of rats in the high-fat control group was 100.0±11.2%, the relative total weight gains of rats in the low dosage group, medium dosage group, and high dosage group were 81.0±10.6%, 72.7±13.4%, and 59.6±12.1%, respectively. Among them, in comparison with the high-fat control group, the relative total weight gains of rats in the low dosage group, medium dosage group, and high dosage group all had reduced significantly (p<0.05), indicating that different dosages of the curcumin-green tea extract complex pharmaceutical composition can all reduce body weight of rats significantly, wherein the weight reduction effect on the high dosage group is the best.

Figure 3B:
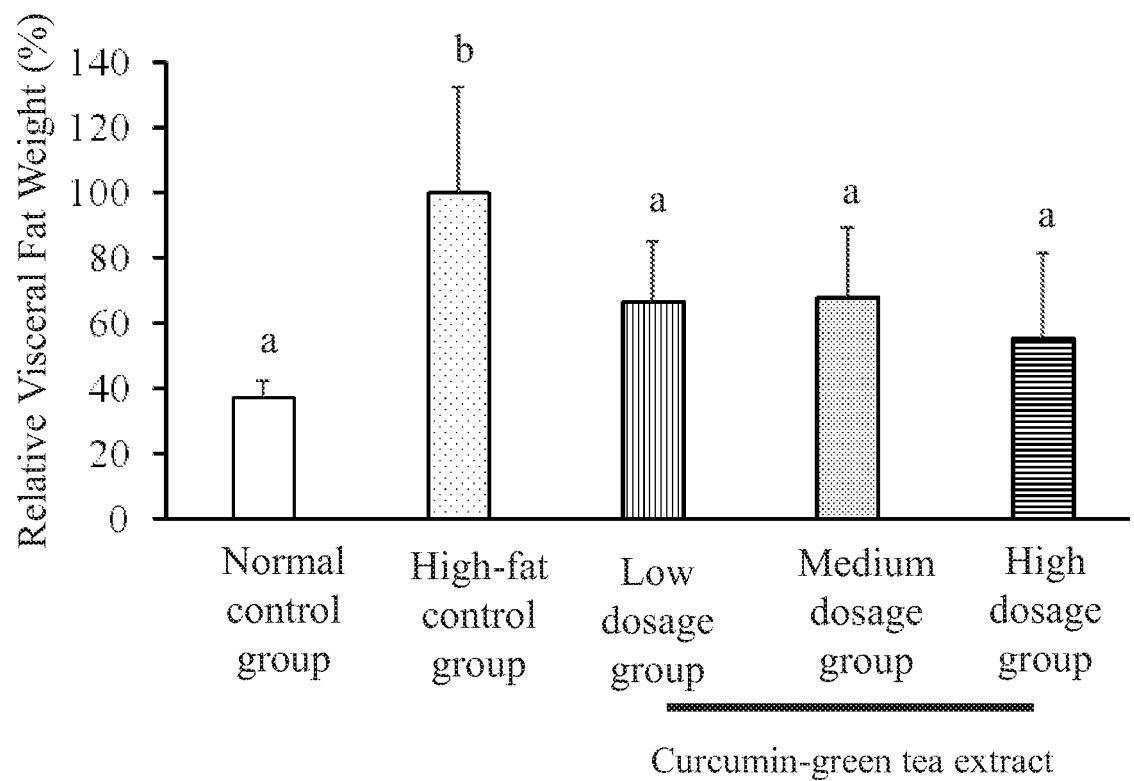
FIG. 3B: A bar graph showing the effect of the dosage of curcumin-green tea extract complex pharmaceutical composition on the relative weight of visceral fat of rats.

Results as shown in FIG. 3B indicate that, the relative visceral fat weight of rats in the normal control group was 37.0±5.2%, the relative visceral fat weight of rats in the high-fat control group was 100.0±32.2%, the relative visceral fat weights of rats in the low dosage group, medium dosage group, and high dosage group were 66.8±18.0%, 68.0±21.0%, and 55.2±26.1%, respectively. Among them, in comparison with the high-fat control group, the relative visceral fat weights of rats in the low dosage group, medium dosage group, and high dosage group could all be reduced significantly (p<0.05), indicating that different dosages of the curcumin-green tea extract complex pharmaceutical composition can all reduce the amount of visceral fat in rats, wherein the effect on the high dosage group is the best.

The experiments above demonstrated that the curcumin-green tea extract complex pharmaceutical composition had significant effect on weight and visceral fat reduction when the dosage of curcumin-green tea extract complex pharmaceutical composition was 10 mg/kg, and the higher the dosage was, the more significant the effect was.

According to the experience of the inventor, when the administered dosage suitable for rats is 10 mg/kg to 40 mg/kg, the administered dosage suitable for humans is 0.1 to 80 mg/kg. Preferably, the administration dosage for humans is 10 to 40 mg/kg.

Preferably, the administration dosage for human is 0.02 to 20 mg/cm$^2$. Preferably, the administration dosage for human is 0.04 to 16 mg/cm$^2$. Preferably, the administration dosage for human is 0.2 to 12 mg/cm². Preferably, the administration dosage for human is 0.4 to 8 mg/cm².

Preferably, the administration dosage for human is 0.01 to 40 mg per kilogram of body weight. Preferably, the administration dosage for human is 0.4 to 40 mg per kilogram of body weight. Preferably, the administration dosage for human is 0.8 to 20 mg per kilogram of body weight.

Experiment 10: Effect of Administration Frequency of Curcumin-Green Tea Extract Complex Pharmaceutical Composition on the Body Weight and Visceral Fat Weight of Rats The preparation of curcumin-green tea extract complex pharmaceutical composition was the same as the procedure of that for the 13' tube in Experiment 8; that is, the ratio of curcumin to green tea extract was 3:2 and the concentration of Cremophor ELP was 15%.

Six-week-old male Sprague-Dawley rats were used for the experiment. 20 rats were fed with normal diet for three days to allow weight to be about 175 to 200 g, and then the rats were assigned into 5 groups, that is, normal control group, high-fat control group, low frequency group, medium frequency group, and high frequency group. Afterwards, the rats in the normal control group were fed with the normal diet continuously for 21 days, and, at the same time, the rats in the high-fat control group, low frequency group, medium frequency group, and high frequency group were fed with high-fat diet for 21 days, to be induced into an obese animal mode to increase body weight up to 400 to 450 g. Thereafter, subcutaneous injections were administered as follows.

Normal control group and High-fat control group: normal saline for injection was administered to rats in the normal control group and high-fat control group via subcutaneous injection, and the administration sites were behind the ear on the back, above the scapula, or below the scapula of rats. One injection per day was administered on the day 1, day 3, day 5, day 7, day 9, day 11, day 13 day, day 15 in the experiment, for a total of 8 injections, and the dosage per injection is 4 mL per kilogram of body weight (4 mL/kg).

Low frequency group: the curcumin-green tea extract complex pharmaceutical composition of the present experiment was administered to the rats via subcutaneous injection, and the administration sites were behind the ear on the back, above the scapula, or below the scapula of rats. One injection per day on the day 1, day 3, day 5, and day 7 in the experiment, for a total of 4 injections, and the dosage per injection is 4 mL per kilogram of body weight (4 mL/kg), to make administration dosage per injection to be 12 mg of curcumin and 8 mg of green tea extract per kilogram of body weight.

Medium frequency group: The way and dosage of injection administration were same as those for the low frequency group, with the only difference in injection frequency. One injection per day was administered on the day 1, day 3, day 5, day 7, day 9, and day 11 in the experiment, for a total of 6 injections.

High frequency group: The way and dosage of injection administrations were same as those for the low frequency group, with the only difference in injection frequency. One injection per day was administered on the day 1, day 3, day 5, day 7, day 9, day 11, day 13, and day 15 in the experiment, for a total of 8 injections.

High fat diet was consistently given during the experiment period, for a duration of 20 days, the rats were sacrifices with $CO_2$ on day 21, and the "relative total weight gain" and "relative visceral fat weight" of rats in each group were calculated.

Figure 4A:
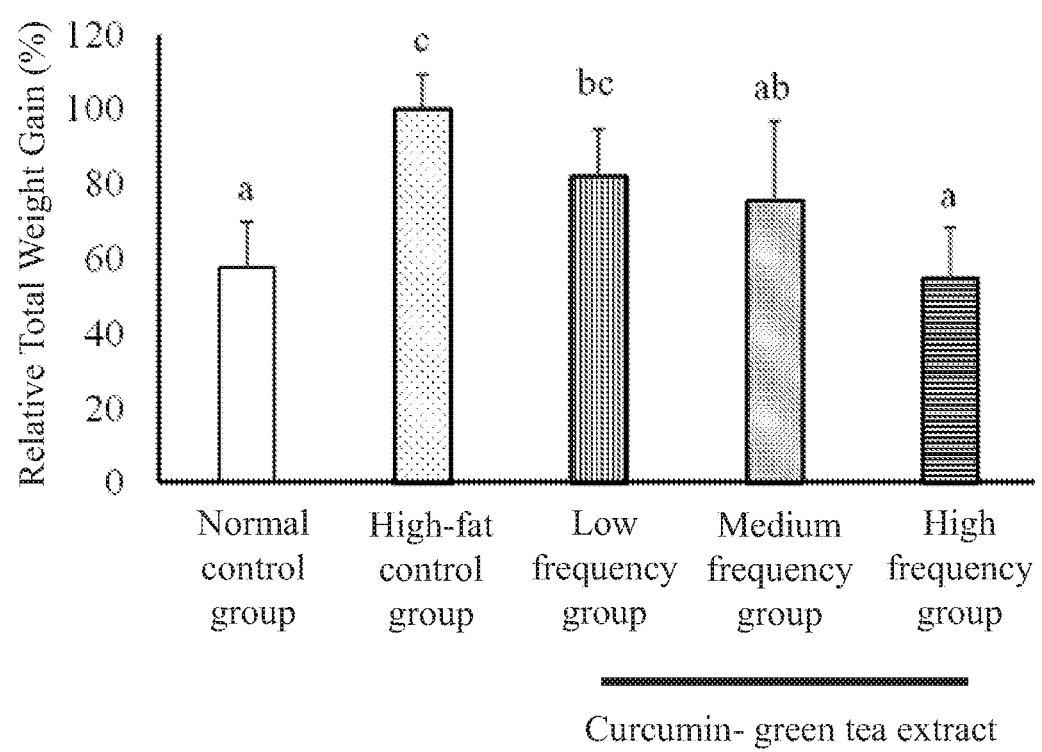
FIG. 4A: A bar graph showing the effect of administration frequency of curcumin-green tea extract complex pharmaceutical composition on the total weight gain of rats.

Results as shown in FIG. 4A indicate that, the relative total weight gain of rats in the normal control was 57.6±12.1%, the relative total weight gain of rats in the high-fat control group was 100.0±9.2%, the relative total weight gains of rats in the low frequency group, medium frequency group, and high frequency group were 82.1±12.3%, 75.7±20.9%, and 54.7±13.4%, respectively. Among them, in comparison with the high-fat control group, the relative total weight gains of rats in the low frequency group, medium frequency group, and high frequency group all reduced significantly ($p<0.05$), indicating that different administration frequencies can all reduce the body weight of rats significantly, wherein the high frequency group has the best weight reduction effect.

Figure 4B:
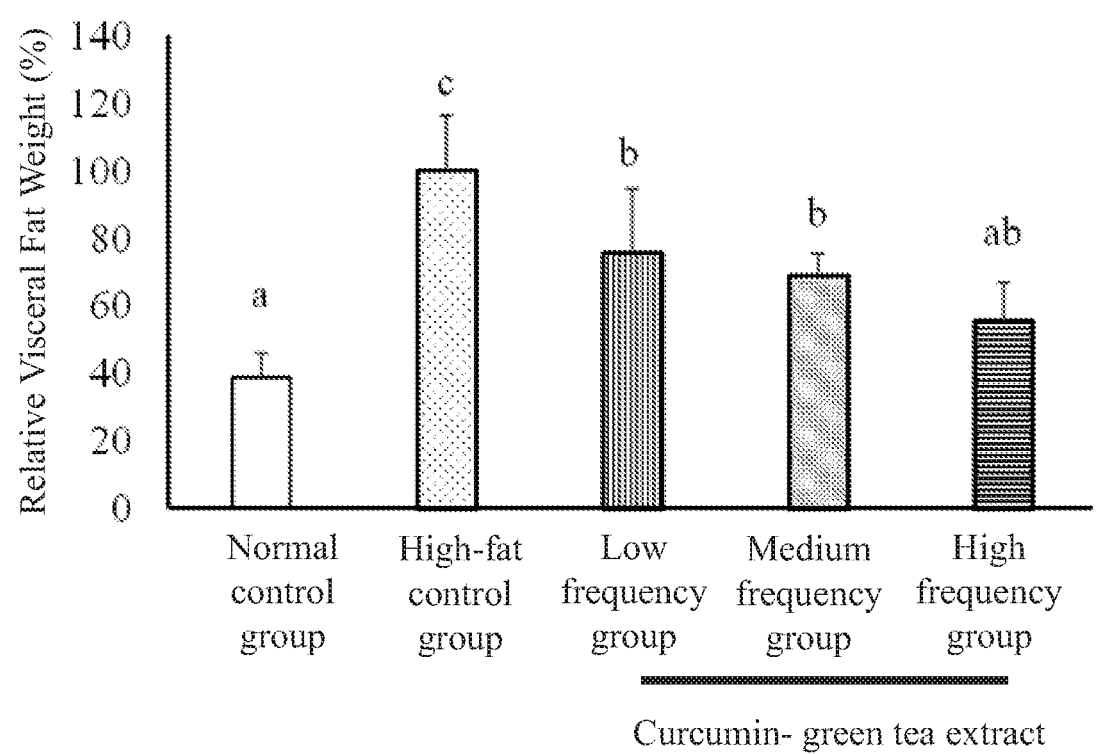
FIG. 4B: A bar graph showing the effect of administration frequency of curcumin-green tea extract complex pharmaceutical composition on the relative weight of visceral fat of rats.

Results as shown in FIG. 4B indicate that, the relative visceral fat weight of rats in the normal control group was 38.7±7.4%, the relative visceral fat weight of rats in the high-fat control group was 100.0±16.2%, the relative visceral fat weights of rats in the low frequency group, medium frequency group, and high frequency group were 75.9±18.5%, 69.0±6.2%, and 55.8±10.9%, respectively. Among them, in comparison with the high-fat control group, the relative visceral fat weights of rats in the low frequency group, medium frequency group, and high frequency group could all be reduced significantly ($p<0.05$), indicating that different frequencies of administration can reduce the visceral fat weight of rats significantly, wherein the high frequency group has the best effect.

The experiments above demonstrated that the curcumin-green tea extract complex pharmaceutical composition had significant effect of weight and internal fat reduction when the administration frequency of curcumin-green tea extract complex pharmaceutical composition is 4 times, and the higher the frequency is, the more significant the effect is.

According to the experience of the inventor, when the administered frequency suitable for rats is 4 to 8 times, the administered frequency suitable for humans is 1 to 16 times. Preferably, the administration frequency suitable for humans is 1 to 6 times.

Preferably, the administration frequency suitable for humans is 1 to 12 times every 1 to 90 days. Preferably, the administration frequency suitable for humans is 1 to 6 times every 1 to 90 days. Or, preferably, the administration frequency suitable for humans is 3 to 60 times every 1 to 90 days; and preferably, the administration frequency suitable for human is 6 to 42 times every 1 to 60 days.

Experiment 11: Effect of Curcumin-Resveratrol Complex Pharmaceutical Composition Administered to Different Groups The curcumin-resveratrol complex pharmaceutical composition in the present experiment was administered to rats fed with normal diet and high-fat diet, respectively, to evaluate the effect of curcumin-resveratrol complex pharmaceutical composition on rats in different groups.

Preparation of curcumin-resveratrol complex pharmaceutical composition: 0.8 g of curcumin, 0.2 g of resveratrol, and 150 to 200 mL of dichloromethane were mixed, and stirred at 150 to 500 rpm at room temperature until curcumin dissolved completely. 30 g of Kolliphor ELP (also known as ELP) was added, and stirred well at 100 to 300 rpm to volatilize the dichloromethane. After the dichloromethane volatilized completely, normal saline for injection was slowly added to reach a total volume of 200 mL. The solution was mixed well to obtain a curcumin-resveratrol complex solution comprising ELP. The curcumin-resveratrol complex solution comprising ELP comprised first and second micelles, the concentration of curcumin was 4 mg/mL, the concentration of resveratrol was 1 mg/mL, and the concentration of Kolliphor ELP (ELP) was approximately 15% (wt %), and the weight ratio of curcumin, resveratrol, and ELP was 4:1:200.

Six-week-old male Sprague-Dawley rats were used for the experiment. 16 rats were fed with normal diet for 1 week to allow weight to be 175 to 200 g, then the rats were assigned into 4 groups, that is, normal diet control group, high-fat diet control group, normal diet-resveratrol complex pharmaceutical composition group, and high-fat diet-resveratrol complex pharmaceutical composition group. Afterwards, the rats in the normal diet control group and normal diet-resveratrol complex pharmaceutical composition group were fed with normal diet continuously for 14 days. At the same time, the rats in the high-fat diet control group and high-fat diet-resveratrol complex pharmaceutical composition were fed with high-fat diet for 14 days, to be induced into an obese animal mode and to increase body weight up to 400 to 450 g. Thereafter, subcutaneous injections were administered as follows.

Normal diet control group and High-fat diet control group: normal saline for injection were administered to the rats via subcutaneous injection, and the administration sites were behind the ear on the back, above the scapula, or below the scapula of rats. One injection per day was administered on the day 1, day 3, day 5, day 7, day 9, and day 11, for a total of 6 injections, and the dosage per injection was 4 mL per kilogram of body weight (4 mL/kg).

Normal diet-resveratrol complex pharmaceutical composition group and high-fat diet-resveratrol complex pharmaceutical composition group: the curcumin-resveratrol complex pharmaceutical composition is administered to the rats via subcutaneous injection, and the administration sites were behind the ear on the back, above the scapula, or below the scapula of rats. One injection per day was administered on the day 1, day 3, day 5, day 7, day 9, day 11, for a total of 6 injections, and the dosage per injection is 4 mL per kilogram of body weight (4 mL/kg) to make the dosage per injection to be 16 mg of curcumin and 4 mg of resveratrol per kilogram of body weight (the total concentration of curcumin and green tea extract administrated per kilogram is 4 mL/kg×5 mg/mL=20 mg/kg, wherein, the weight ratio of curcumin to resveratrol is 4:1, hence the administered curcumin per kilogram of body weight is 20 mg/kg÷5×4=16 mg, and the administered resveratrol per kilogram of body weight is 20 mg/kg÷5×1=4 mg).

Normal diet was given consistently to the rats in the normal diet control group and normal diet-resveratrol complex pharmaceutical composition group during the experiment, and high-fat diet was given to the rats in the high-fat diet control group and high-fat diet-resveratrol complex pharmaceutical composition group. The experiment performed for a total of 20 days, and the rats were sacrificed with $CO_2$ on day 21.

Experimental results indicate that, in comparison with the normal diet control group, the relative visceral fat weight of the rats in the normal diet-resveratrol complex pharmaceutical composition did not reduced significantly, indicating that the pharmaceutical composition of the present invention cannot reduce body weight of normal rats, and cannot reduce visceral fat weight of normal rats. In comparison with the high-fat diet control group, the relative total weight gain and the relative visceral fat weight of the rats in the high-fat diet-resveratrol complex pharmaceutical composition group had all reduced significantly ($p<0.05$), indicating that the pharmaceutical composition of the present invention can reduce body weight of overweight or obese rats, and can also reduce the visceral fat weight of overweight or obese rats.

The experiments above demonstrated that the pharmaceutical composition of the present invention can only have the effect of body weight and visceral fat reduction on certain groups, that is, can only take the effect of body weight and visceral fat reduction on groups of overweight or obese.

Experiment 12: Effect of Different Ratios of Curcumin-Resveratrol Complex Composition on the Body Weight and Visceral Fat Weight of Rats The curcumin-resveratrol complex pharmaceutical composition in the present invention were divided into 12 tubes, that is, the curcumin tube, resveratrol tube, and the 1" to 10" tube, and the preparation of composition in each tube was substantially the same as the experimental procedure in Experiment 11. The only differences were the ratios of curcumin to resveratrol. Furthermore, the concentration of Kolliphor ELP was 15%. The ratios of curcumin to resveratrol are as shown in Table 7.

TABLE 7

The weight ratios and total concentrations of curcumin to resveratrol in the curcumin-resveratrol complex pharmaceutical compositions

| Tube | Ratio of Curcumin to Resveratrol (Weight Ratio) | Total Concentration of Curcumin and Resveratrol (mg/mL) |
| --- | --- | --- |
| Curcumin | 1:0 | |
| Resveratrol | 0:1 | |
| 1" | 50:1 | 5 |
| 2" | 20:1 | 5 |
| 3" | 15:1 | 5 |
| 4" | 8:1 | 5 |
| 5" | 4:1 | 5 |
| 6" | 1:1 | 5 |
| 7" | 1:4 | 5 |
| 8" | 1:10 | 5 |
| 9" | 1:20 | 5 |
| 10" | 1:30 | 5 |

Six-week-old male Sprague-Dawley rats were used for the experiment. 52 rats were fed with normal diet for three days to allow weight to be 175 to 200 g, and then fed with high-fat diet for 21 days to be induced into an obese animal mode and to increase body weight up to 400 to 450 g. The rats were divided randomly into 13 groups, that is, high-fat control group, curcumin group, resveratrol group, and the OIR1 to OIR10 group, respectively, with four rats per group, and there was no statistical difference for the weight in each group of rats. Subcutaneous injections were administered as follows.

High-fat control group: normal saline for injection was administered to high-fat control rats via subcutaneous injection, and the administration sites were behind the ear on the back, above the scapula, or below the scapula of rats. One injection per day was administered on the day 1, day 3, day 5, day 7, day 9, day 11, for a total of 6 injections, and the dosage per injection is 4 mL per kilogram of body weight (4 mL/kg).

Curcumin group, Resveratrol group, and the OIR1 to OIR10 group: the pharmaceutical compositions in the curcumin tube, the resveratrol tube, and the 1" to 10" tube were administered to the rats in the curcumin group, the resveratrol group, and the OIR1 to OIR10 group, respectively, and the administration sites were behind the ear on the back, above the scapula, or below the scapula of rats. One injection per day was administered on the day 1, day 3, day 5, day 7, day 9, and day 11, for a total of 6 injections, and the dosage per injection was 4 mL per kilogram of body weight (4 mL/kg) to make the dosage per injection to be 20 mg per kilogram of bodyweight (The total concentration of curcumin and resveratrol administered per kilogram of body weight is 4 mL/kg×5 mg/mL=20 mg/kg).

High-fat diet was consistently given during the experiment period, for a duration of 20 days, the rats were sacrificed with $CO_2$ on day 21, and the "relative total weight gain" and "relative visceral fat weight" were calculated.

Figure 5A:
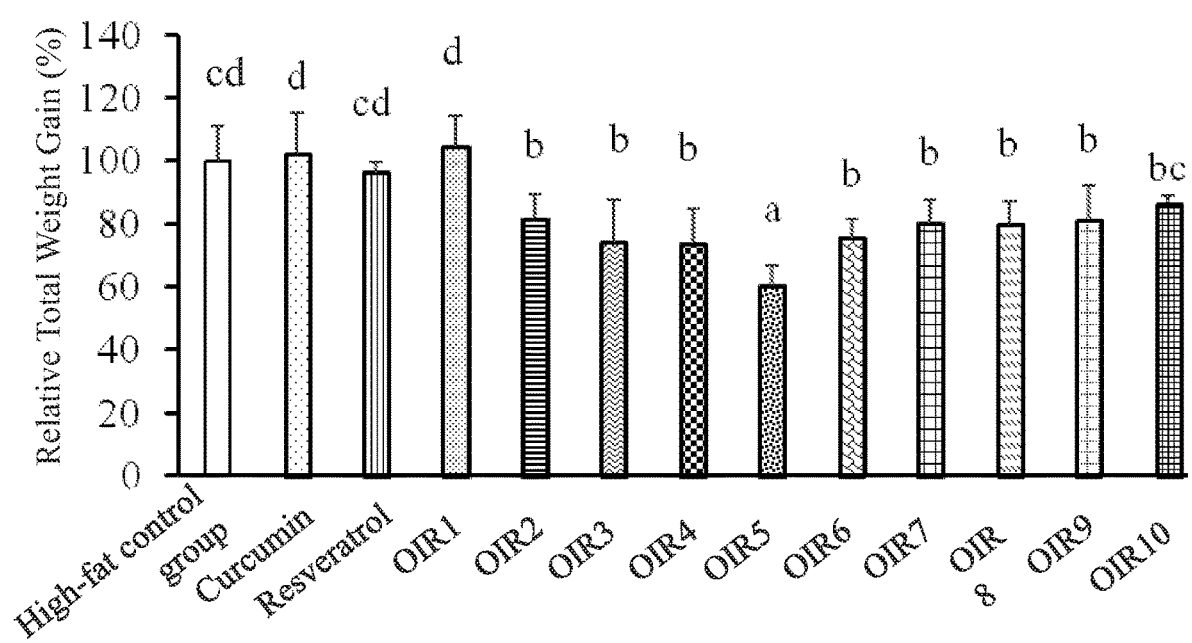
FIG. 5A: A bar graph showing the effect of the ratio of curcumin to resveratrol on the relative total weight gain of rats.

Results as shown in FIG. 5A indicate that, the relative total weight gain of the rats in the high-fat control group was 100.0±11.1%, the relative total weight gain of the rats in the curcumin group was 102.4±13%, the relative total weight gain of the rats in the resveratrol group was 96.3±3.2%, and the relative total weight gains of the rats in the OIR1 to OIR10 group were 104.4±9.7%, 81.7±7.6%, 74.2±13.4%, 73.7±11.2%, 60.4±6.3%, 75.4±6.1%, 80.2±7.1%, 79.5±7.5%, 80.9±11.2%, and 86.3±2.8%, respectively. Among them, in comparison with the high-fat control group, the differences of relative total weight gains of rats in the curcumin group and the resveratrol group did not reduced significantly ($p>0.05$), indicating that if solely curcumin or resveratrol is provided, the weight of rat cannot be reduced significantly under the conditions of the present experiment. However, in comparison with the high-fat control group, the relative total weight gains of rats in the OIR2 to OIR9 group all had reduced significantly ($p<0.05$), indicating that when the ratio of curcumin to resveratrol is in the range of 20:1 to 1:20, the body weight of rat can be reduced significantly. Furthermore, in comparison with the curcumin group or the resveratrol group, the relative total weight gains of the rats in the OIR2 to OIR9 group had all reduced significantly ($p<0.05$), indicating that when the ratio of curcumin to resveratrol is in the range of 20:1 to 1:20, synergy is present. Preferably, when the ratio of curcumin to resveratrol is 4:1, preferred synergy is present.

Figure 5B:
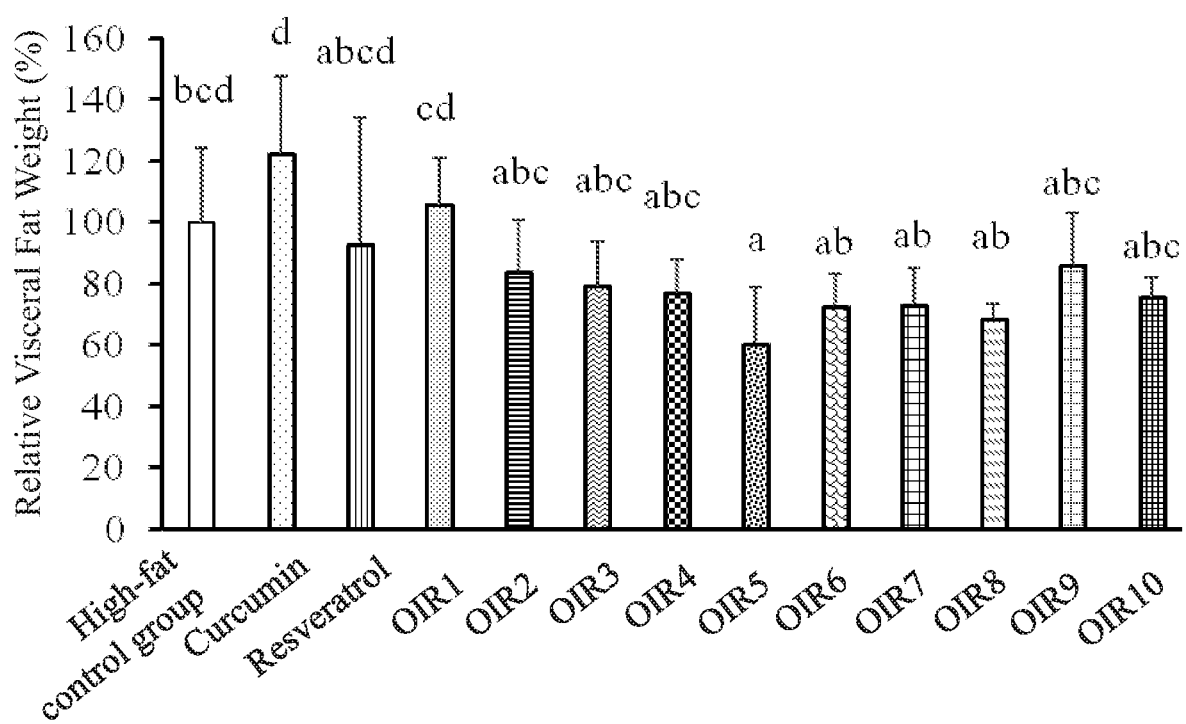
FIG. 5B: A bar graph showing the effect of the ratio of curcumin to resveratrol on the relative visceral fat of rats.

Results as shown in FIG. 5B indicate that, the relative visceral fat weight of the rats in the high-fat control group was 100.0±24.2%, the relative visceral fat weight of the rats in the curcumin group was 122.2±25.2%, the relative visceral fat weight of the rats in the resveratrol group was 92.5±41.7%, and the relative visceral fat weight of the rats in the OIR1 to OIR10 group were 105.8±15.4%, 83.6±17.1%, 79.4±14%, 76.9±11%, 60.5±18.2%, 72.7±10.4%, 73±12.1%, 68.4±5.2%, 86.1±17.1%, and 75.8±6.3%, respectively. Among them, in comparison with the high-fat control group, the relative visceral fat weight of the rats in the curcumin group and the resveratrol extract group did not reduce significantly ($p>0.05$), indicating that solely providing curcumin or resveratrol cannot reduce visceral fat in the rats significantly under the conditions of the present experiment. However, in comparison with the curcumin and resveratrol group, the relative visceral fat weight of the rats in the OIR2 to OIR10 group had a trend to further reduction, indicating that at the same total drug concentration, collective administration of curcumin and resveratrol to rats can facilitate achieving the effect of reducing the amount of visceral fat of rat.

Experiment 13: Effects of Different Dosages of Curcumin-Resveratrol Complex Composition on the Body Weight and Visceral Fat Weight of Rats The preparation of the curcumin-resveratrol complex pharmaceutical composition of the present experiment was the same as the procedure of the composition in the 5" tube in Experiment 12, that is, the ratio of curcumin to resveratrol is 4:1 and the concentration of Kolliphor ELP is 15%.

Six-week-old male Sprague-Dawley rats were used for the experiment. 20 rats were fed with normal diet for three days to allow weight to be about 175 to 200 g, and then the rats were assigned into 5 groups, that is, normal control group, high-fat control group, low dosage group, medium dosage group, and high dosage group. Afterwards, the rats in the normal control group were continuously fed with normal diet for 21 days. At the same time, the rats in the high-fat control group, low dosage group, medium dosage group, and high dosage group were fed with high-fat diet for 21 days to be induced into an obese animal mode and to increase body weight up to 400 to 450 g. Thereafter, subcutaneous injections were administered as follows.

Normal control group and High-fat control group: normal saline for injection was administered to the rats in the normal control group and the high-fat control group via subcutaneous injection, and the administration sites are behind the ear on the back, above the scapula, or below the scapula of rats. One injection per day was administered on the day 1, day 3, day 5, day 7, day 9, day 11, for a total of 6 injections, and the dosage per injection was 8 mL per kilogram of body weight (8 mL/kg).

Low dosage group: the curcumin-resveratrol complex pharmaceutical composition of the present invention was administered to the rats via subcutaneous injection, and the administration sites were behind the ear on the back, above the scapula, or below the scapula of rats. One injection per day was administered on the day 1, day 3, day 5, day 7, day 9, and day 11, for a total of 6 injections, and the dosage per injection is to inject 2 mL per kilogram of body weight (2 mL/kg) to make the dosage per injection to be 8 mg of curcumin and 2 mg of resveratrol per kilogram of body weight.

Medium dosage group: The way and frequency of administration were the same as those for the low dosage group, with the only difference in injection dosage. The dosage per injection is to inject 4 mL per kilogram of body weight (4 mL/kg), to make the dose per injection to be 16 mg of curcumin and 4 mg of resveratrol per kilogram of body weight.

High dosage group: The way and frequency of administration were the same as those for the low dosage group, with the only difference in injection dosage. The dosage per injection is to inject 8 mL per kilogram of body weight (8 mL/kg), to make the dose per injection to be 32 mg of curcumin and 8 mg of resveratrol per kilogram of body weight.

High fat diet was consistently given during the experiment period, for a duration of 20 days and the rats were sacrificed with $CO_2$ on day 21. The "relative total weight gain" and "relative visceral fat weight" of the rats in each group were calculated.

Figure 6A:
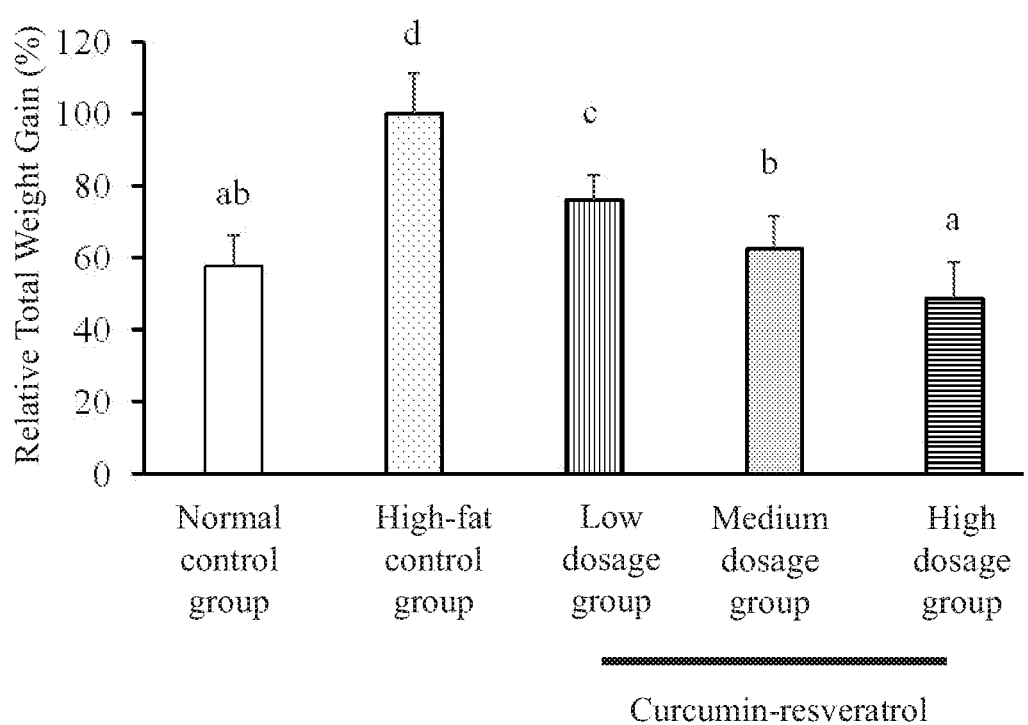
FIG. 6A: A bar graph showing the effect of the dosage of curcumin-resveratrol complex pharmaceutical composition on the relative total weight gain of rats.

Results as shown in FIG. 6A indicate that, the relative total weight gain of the rats in the normal control group was 57.4±8.6%, the relative total weight gain of the rats in the high-fat control group was 100.0±11.2%, the relative total weight gains of the rats in the low dosage group, medium dosage group, and high dosage group were 76.2±6.7%, 62.4±9.1% and 48.7±10.1%, respectively. Among them, in comparison with the high-fat control group, the relative total weight gains of rats in the low dosage group, medium dosage group, and high dosage group all reduced significantly (p<0.05), indicating that different dosages of the curcumin-resveratrol complex pharmaceutical composition can all reduce body weight of rats significantly, wherein the weight reduction effect on the high dosage group is the best.

Figure 6B:
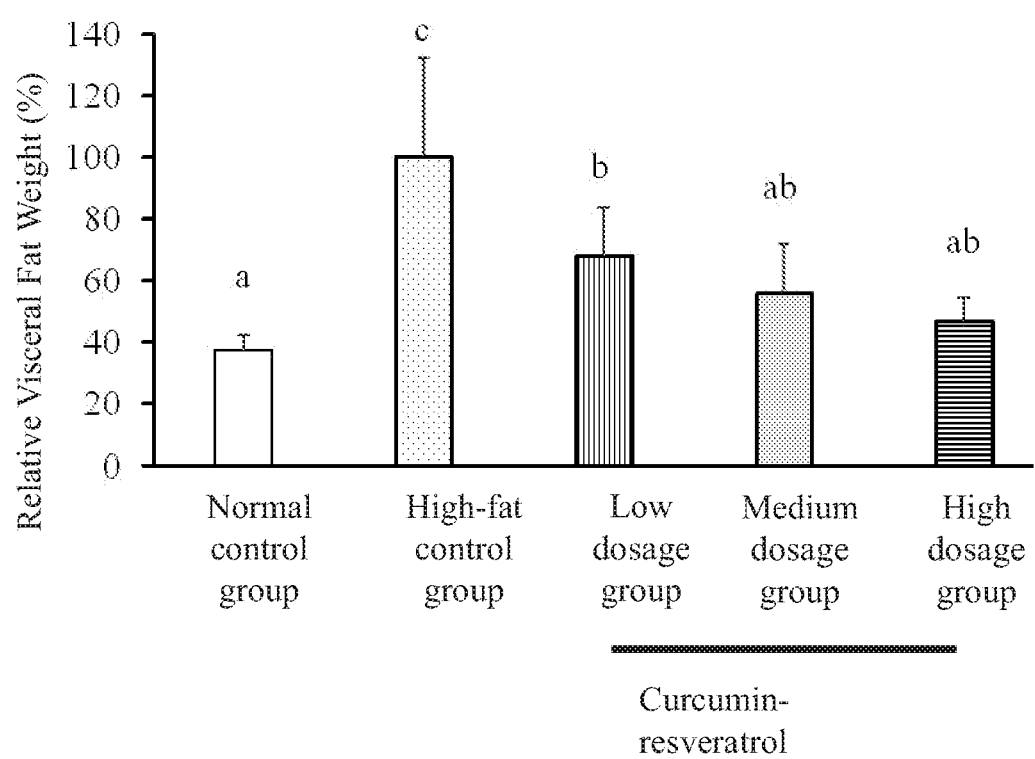
FIG. 6B: A bar graph of the effect of the dosage of curcumin-resveratrol complex pharmaceutical composition on the relative weight of visceral fat of rats.

Results as shown in FIG. 6B indicate that, the relative visceral fat weight of the rats in the normal control group was 37.0±5.2%, the relative visceral fat weight of the rats in the high-fat control group was 100.0±32.2%, the relative visceral fat weights of the rats in the low dosage group, medium dosage group, and high dosage group were 68.1±15.2%, 56.0±15.7%, and 46.9±7.2%, respectively. Among them, in comparison with the high-fat control group, the relative visceral fat weights of the rats in the low dosage group, medium dosage group, and high dosage group all reduced significantly (p<0.05), indicating that different dosages of the curcumin-resveratrol complex pharmaceutical composition can all effectively reduce the weight of visceral fat of rats, wherein the high dosage group has the best effect.

The above experiments demonstrated that, the curcumin-resveratrol complex pharmaceutical composition has significant effect of weight reduction and visceral fat reduction, when the dosage of curcumin-resveratrol complex pharmaceutical composition is 10 mg/kg, and the higher the dosage is, the more significant the effect is.

According to the experience of the inventor, when the administered dosages suitable for rats are 10 mg/kg to 40 mg/kg, the administered dosages suitable for humans are 0.1 to 80 mg/kg. Preferably, the administration dosage for humans is 10 to 40 mg/kg.

Preferably, the administration dosage for humans is to inject 0.02 to 20 mg per $cm^2$. Preferably, the administration dosage for humans is to inject 0.04 to 16 mg per $cm^2$. Preferably, the administration dosage for humans is to inject 0.2 to 12 mg per $cm^2$. Preferably, the administration dosage for humans is to inject 0.4 to 8 mg per $cm^2$.

Preferably, the administration dosage for humans is to inject 0.01 to 40 mg per kilogram. Preferably, the administration dosage for humans is to inject 0.4 to 40 mg per kilogram. Preferably, the administration dosage for humans is to inject 0.8 to 20 mg per kilogram.

Experiment 14: Effect of Administration Frequency of Curcumin-Resveratrol Complex Composition on the Body Weight and Visceral Fat Weight of Rats The preparation of curcumin-resveratrol complex pharmaceutical composition of the present experiment was the same as the procedure of the 5" tube in Experiment 12, this is, the ratio of curcumin to resveratrol was 4:1 and the concentration of Cremophor ELP was 15%.

Six-week-old male Sprague-Dawley rats were used for the experiment. 20 rats were fed with normal diet for three days to allow weight to be 175 to 200 g, and then the rats were assigned into 5 groups, that is, normal control group, high-fat control group, low frequency group, medium frequency group, and high frequency group. Afterwards, the rats in the normal control group were fed with normal diet continuously for 21 days. At the same time, the rats in the high-fat control group, low frequency group, medium frequency group, and high frequency group were fed with high-fat diet continuously for 21 days, to be induced into an obese animal mode and to increase body weight up to 400 to 450 g. Thereafter, subcutaneous injections were administered as follows.

Normal control group and High-fat control group: normal saline for injection was administered to the rats in the normal control group and the high-fat control group via subcutaneous injection, and the administration sites were behind the ear on the back, above the scapula, or below the scapula of rats. One injection per day was administered on the day 1, day 3, day 5, day 7, day 9, day 11, day 13, and day 15, for a total of 8 injections, and the dosage per injection is 4 mL per kilogram of body weight (4 mL/kg).

Low frequency group: the curcumin-resveratrol complex pharmaceutical composition of the present experiment was administered to the rats via subcutaneous injection, and the administration sites were behind the ear on the back, above the scapula, or below the scapula of rats. One injection per day was administered on the day 1, day 3, day 5, and day 7 in the experiment, for a total of 4 injections, and the dosage per injection was 4 mL per kilogram of body weight (4 mL/kg), to make administration dosage per injection to be 16 mg of curcumin and 4 mg of resveratrol per kilogram of body weight.

Medium frequency group: The way and dosage of administration were same as those for the low frequency group, with the only difference in administering frequency. Administration was performed once per day on the day 1, day 3, day 5, day 7, day 9, and day 11 in the experiment, for a total of 6 times of administration.

High frequency group: The way and dosage of administration are same as those for the low frequency group, with the only difference in administering frequency. Administration was performed once per day on the day 1, day 3, day 5, day 7, day 9, day 11, day 13, and day 15 in the experiment, for a total of 8 times of administrations.

High fat diet was consistently given during the experiment period, for a duration of 20 days, the rats were sacrificed with $CO_2$ on day 21, and the "relative total weight gain" and "relative visceral fat weight" of rats were calculated in each group.

Figure 7A:
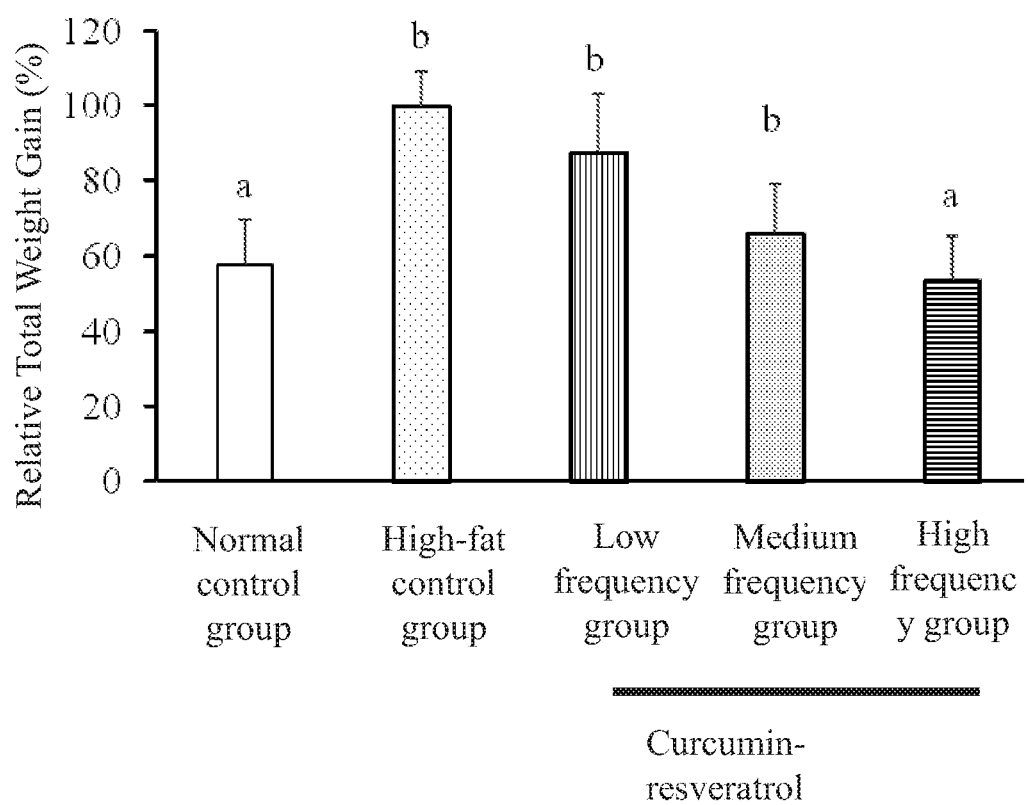
FIG. 7A: A bar graph of the effect of administration frequency of curcumin-resveratrol complex pharmaceutical composition on the relative total weight gain of rats.

Results as shown in FIG. 7A indicate that, the relative total weight gain of the rats in the normal control group was 57.6±12.1%, the relative total weight gain of the rats in the high-fat control group was 100.0±9.2%, the relative total weight gains of the rats in the low frequency group, medium frequency group, and high frequency group were 87.5±15.8%, 66.2±13.0%, and 53.7±11.7%, respectively. Among them, in comparison with the high-fat control group, the relative total weight gain of the rats in the high frequency group had reduced significantly (p<0.05), indicating that the body weight of rat can be significantly reduced when the administering frequency is 8 times.

Figure 7B:
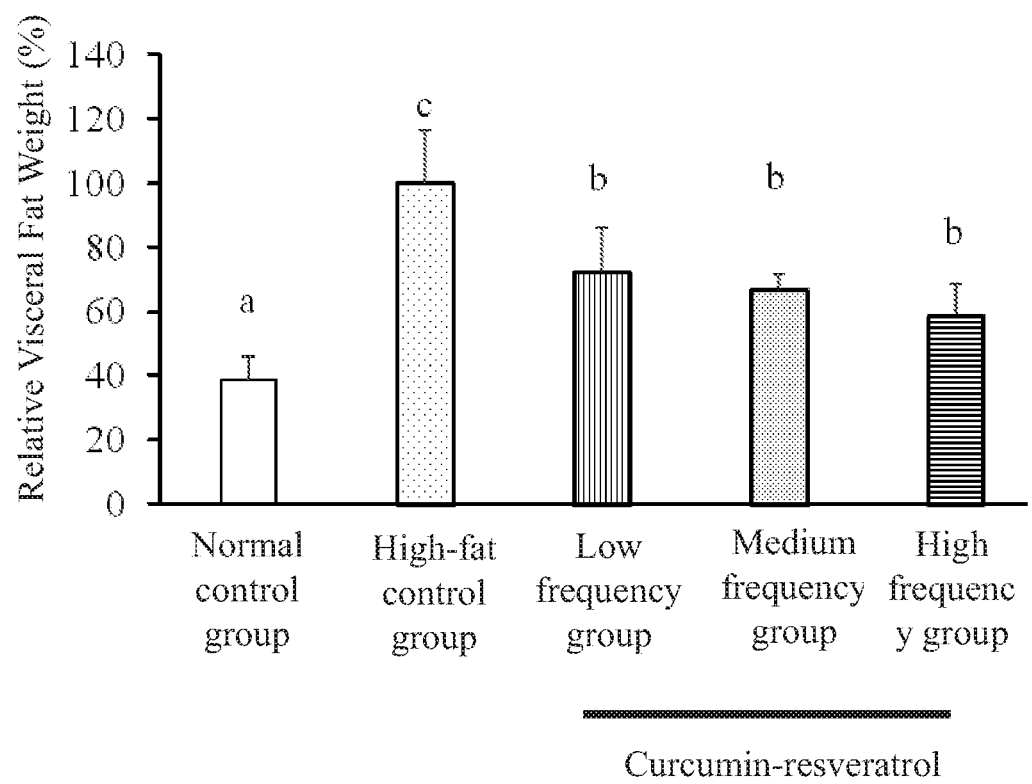
FIG. 7B: A bar graph of the effect of administration frequency of curcumin-resveratrol complex pharmaceutical composition on the relative weight of visceral fat of rats.

Results as shown in FIG. 7B indicate that, the relative visceral fat weight of the rats in the normal control group was 38.7±7.4%, the relative visceral fat weight of the rats in the high-fat control group was 100.0±16.2%, the relative visceral fat weights of the rats in the low frequency group, medium frequency group, and high frequency group were 72.2±13.7%, 66.8±4.5%, and 58.6±10.0%, respectively. Among them, in comparison with the high-fat control group, the relative visceral fat weight of the rats in the low frequency group, medium frequency group, and high frequency group all reduced significantly (p<0.05), indicating that different administering frequencies all can reduce the amount of visceral fat of rat significantly, wherein the effect of high frequency group is the best.

The above experiments demonstrated that, the curcumin-resveratrol complex pharmaceutical composition has the significant effect of reducing visceral fat when the administration frequency is four times, and the significant effect on reducing weight can be achieved when the administration frequency is eight times.

According to the experience of the inventor, when the administration frequency suitable for rats is 4 to 8 times, the administration frequency suitable for humans is 1 to 16 times. Preferably, the administration frequency of the administration for humans is 1 to 6 times.

Preferably, the administration frequency for humans is 1 to 12 times per 1 to 90 days. Preferably, the administration frequency for humans is 1 to 6 times per 1 to 90 days. Or, preferably, the administration frequency for humans is 3 to 60 times per 1 to 90 days; preferably, the administration frequency for humans is 6 to 42 times per 1 to 60 days.

As demonstrated by the examples of the present invention, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic (water soluble) drug complex pharmaceutical composition provided by the present invention, and other pharmaceutical compositions provided by the present invention can all reduce body weight and the amount of visceral fat. Therefore, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition provided by the present invention, and other pharmaceutical compositions provided by the present invention can be used to prepare subcutaneous implanted devices, subcutaneous implants, solutions for implanted infusion, cream, or patches, which is capable of being administered to the subject to reduce the body weight or body fat of the subject.

Preferably, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition provided by the present invention, and other pharmaceutical compositions provided by the present invention can reduce the body weight or body fat of a subject by subcutaneous injection or subcutaneous fat injection. Thus, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition, and other pharmaceutical compositions provided by the present invention can be used to prepare subcutaneous fat layer injection formulation or subcutaneous injection formulation for reducing body weight or body fat.

The foregoing descriptions are merely the preferred embodiments of the present invention and are not intended to limit the scope of patent application of the present invention. Therefore, any alteration or modification that does not depart from the spirits disclosed herein should be included within the scope of patent application of the present invention.

What is claimed is:

1. A method of reducing the body weight of an overweight human or an obese human in need thereof, consisting essentially of administering a therapeutically effective amount of a subcutaneous injection formulation to the overweight human or obese human, wherein the subcutaneous injection formulation consists essentially of:
    a) a curcuminoid; and
    b) polyoxyl-35 castor oil, PEG-40 hydrogenated castor oil or 2-hydroxyethyl 12-hydroxyoctadecanoate;
    wherein the polyoxyl-35 castor oil, PEG-40 hydrogenated castor oil or 2-hydroxyethyl 12-hydroxyoctadecanoate and the curcuminoid form a plurality of curcuminoid-containing micelles, which encapsulate the curcuminoid;
    wherein a total concentration of the curcuminoid in the curcuminoid-containing micelles is 0.2 to 167 mg/g;
    wherein the weight ratio of the curcuminoid to the polyoxyl-35 castor oil, PEG-40 hydrogenated castor oil or 2-hydroxyethyl 12-hydroxyoctadecanoate is 1:20 to 1:150; and
    wherein the body weight of the overweight human or the obese human in need thereof is effectively reduced.
2. The method of claim 1, wherein the curcuminoid is curcumin.
3. The method of claim 2, wherein the total concentration of the curcuminoid in the curcuminoid-containing micelles is 0.4 to 167 mg/g.
4. The method of claim 2, wherein the total concentration of the curcuminoid in the curcuminoid-containing micelles is 0.5 to 111 mg/g.
5. The method of claim 2, wherein the total concentration of the curcuminoid in the curcuminoid-containing micelles is 2 to 91 mg/g.
6. The method of claim 2, wherein the subcutaneous injection formulation further consists essentially of a catechin.
7. The method of claim 6, wherein the concentration of the catechin is 0.04 to 835 mg/g.
8. The method of claim 7, wherein the concentration of the catechins is 0.15 to 733 mg/g.
9. The method of claim 6, wherein the catechin is selected from the group consisting of epigallocatechin gallate, epicatechin, epicatechin gallate, epigallocatechin, gallocatechin gallate, gallocatechin, catechin gallate, and a combination thereof.
10. The method of claim 3, wherein the weight ratio of the curcuminoid to the catechin in the subcutaneous injection formulation is 50:1 to 1:20.
11. The method of claim 10, wherein the weight ratio of the curcuminoid to the catechin in the subcutaneous injection formulation is 30:1 to 1:10.
12. The method of claim 11, wherein the weight ratio of the curcuminoid to the catechins in the subcutaneous injection formulation is 10:1 to 1:4.
13. The method of claim 11, wherein the weight ratio of the curcuminoid to the catechins in the subcutaneous injection formulation is 7:1 to 1:4.
14. The method of claim 2, wherein the therapeutically effective amount of the subcutaneous injection formulation is 0.15 to 40 milligram per kilogram for injection into the human in need thereof.
15. The method of claim 14, wherein the therapeutically effective amount of the subcutaneous injection formulation is 0.25 to 25 milligram per kilogram for injection into the human in need thereof.

16. The method of claim 2, wherein the administration frequency of the subcutaneous injection formulation at an administration site of the human in need thereof is 1 to 6 times every 1 to 90 days.

17. The method of claim 2, wherein the subcutaneous injection formulation further consists essentially of:
a) a cosolvent selected from the group consisting of polyethylene, glycol, propylene glycol, and ethanol;
b) a suspending agent selected from the group consisting of sodium alginate, glycerol, carboxymethylcellulose sodium, and mannitol; and
c) an oil phase excipient selected from the group consisting of oleic acid, castor oil, sesame oil, cottonseed oil, soybean oil, safflower oil, corn oil, glycerol, and a combination thereof.

18. The method of claim 17, wherein the subcutaneous injection formulation further consists essentially of the cosolvent, the oil phase excipient, the suspending agent, or a combination thereof.

19. The method of claim 2, wherein the subcutaneous injection formulation further consists essentially of resveratrol, wherein the polyoxyl-35 castor oil, PEG-40 hydrogenated castor oil or 2-hydroxyethyl 12-hydroxyoctadecanoate and the resveratrol form a plurality of resveratrol-containing micelles, which encapsulate the resveratrol.

20. The method of claim 19, wherein the total concentration of the resveratrol encapsulated in the resveratrol-containing micelles is 0.2 to 733 mg/g.

21. The method of claim 19, wherein the total concentration of the curcuminoid encapsulated in the curcuminoid-containing micelles and of the resveratrol encapsulated in the resveratrol-containing micelles is 0.4 to 900 mg/g.

22. The method of claim 19, wherein the ratio of the total weight of the curcuminoid encapsulated in the curcuminoid-containing micelles to the total weight of the resveratrol encapsulated in the resveratrol-containing micelles is 50:1 to 1:30.

23. The method of claim 22, wherein the ratio of the total weight of the curcuminoid encapsulated in the curcuminoid-containing micelles to the total weight of the resveratrol encapsulated in the resveratrol-containing micelles is 20:1 to 1:20.

* * * * *